United States Patent
Wang et al.

(10) Patent No.: US 11,047,935 B2
(45) Date of Patent: Jun. 29, 2021

(54) SYSTEMS AND METHODS FOR ESTIMATING COMPLEX B1+ FIELDS OF TRANSMIT COILS OF A MAGNETIC RESONANCE IMAGING (MRI) SYSTEM

(71) Applicant: OHIO STATE INNOVATION FOUNDATION, Columbus, OH (US)

(72) Inventors: Jinghua Wang, Columbus, OH (US); Yu Ding, Sugar Land, TX (US)

(73) Assignee: Ohio State Innovation Foundation, Columbus, OH (US)

( * ) Notice: Subject to any disclaimer, the term of this patent is extended or adjusted under 35 U.S.C. 154(b) by 298 days.

(21) Appl. No.: 15/573,918

(22) PCT Filed: May 16, 2016

(86) PCT No.: PCT/US2016/032671
§ 371 (c)(1),
(2) Date: Nov. 14, 2017

(87) PCT Pub. No.: WO2016/183572
PCT Pub. Date: Nov. 17, 2016

(65) Prior Publication Data
US 2018/0246178 A1    Aug. 30, 2018

Related U.S. Application Data

(60) Provisional application No. 62/161,569, filed on May 14, 2015.

(51) Int. Cl.
*A61B 5/055* (2006.01)
*G01R 33/24* (2006.01)
(Continued)

(52) U.S. Cl.
CPC ............ *G01R 33/246* (2013.01); *A61B 5/055* (2013.01); *G01R 33/5612* (2013.01); *G01R 33/5659* (2013.01); *G01V 3/14* (2013.01)

(58) Field of Classification Search
CPC .............. G01R 33/246; G01R 33/5612; G01R 33/5659; A61B 5/055; G01V 3/14
See application file for complete search history.

(56) References Cited

U.S. PATENT DOCUMENTS 5,001,428 A    3/1991    Maier et al.
6,268,728 B1   7/2001    Morrell
(Continued)

FOREIGN PATENT DOCUMENTS

WO    2005078470    8/2005
WO    2009118688    10/2009
(Continued)

OTHER PUBLICATIONS

Zhang,X.T., Liu, J., He,B., "Magnetic resonance based electrical properties tomography: a review." IEEE Rev Biomed Eng, 7, pp. 87-96 (Year: 2014).*
(Continued)

*Primary Examiner* — Bill Thomson
*Assistant Examiner* — Amal Aly Farag
(74) *Attorney, Agent, or Firm* — Meunier Carlin & Curfman LLC

(57) ABSTRACT

Systems and methods for estimating complex transmit field $B_1^+$ a transmit coil of a magnetic resonance imaging (MRI) system in both k-space and image domains are described herein. Estimating complex RF field $B_1^+$ in the k-space domain includes acquiring complex data in a k-space domain, estimating a complex $B_1^+$ map in the k-space domain of a transmit coil and storing the complex $B_1^+$ map. The complex $B_1^+$ map can be estimated based on the complex images. Estimating complex transmit field $B_1^+$ in the image domain includes acquiring at least two complex images in a k-space domain, transforming the complex images into an image domain, estimating a complex $B_1^+$ (Continued)

map in the image domain of a transmit coil, and storing the complex $B_1^+$ map.

21 Claims, 7 Drawing Sheets

(51) Int. Cl.
  *G01R 33/561* (2006.01)
  *G01R 33/565* (2006.01)
  *G01V 3/14* (2006.01)

(56) References Cited

U.S. PATENT DOCUMENTS

| | | | |
|---|---|---|---|
| 6,552,538 | B2 | 4/2003 | Demeester et al. |
| 7,064,546 | B2 | 6/2006 | Feiweier |
| 7,446,526 | B2 | 11/2008 | Cunningham et al. |
| 7,603,158 | B2 | 10/2009 | Nachman et al. |
| 7,768,264 | B1 | 8/2010 | Brau et al. |
| 7,795,870 | B2 | 9/2010 | Sodickson et al. |
| 7,839,147 | B2 | 11/2010 | Katscher et al. |
| 7,859,262 | B2 | 12/2010 | Jellus |
| 8,026,720 | B1 | 9/2011 | Chen et al. |
| 8,054,078 | B2 | 11/2011 | Ikezaki |
| 8,076,939 | B2 | 12/2011 | Setsompop et al. |
| 8,077,955 | B2 | 12/2011 | Dannels et al. |
| 8,125,225 | B2 | 2/2012 | Koretsky |
| 8,148,984 | B2 | 4/2012 | Johnson et al. |
| 8,198,891 | B2 | 6/2012 | Sacolick et al. |
| 8,258,786 | B2 | 9/2012 | Hennel |
| 8,305,077 | B2 | 11/2012 | Morrell et al. |
| 8,427,156 | B2 | 4/2013 | Kholmovski et al. |
| 8,446,149 | B2 | 5/2013 | Heberlein et al. |
| 8,502,534 | B2 | 8/2013 | Lai et al. |
| 8,502,538 | B2 | 8/2013 | Dannels et al. |
| 8,558,547 | B2 | 10/2013 | Sacolick et al. |
| 8,736,265 | B2 | 5/2014 | Boernert et al. |
| 8,805,042 | B2 | 8/2014 | Weiss |
| 8,831,318 | B2 | 9/2014 | Sharif et al. |
| 8,891,846 | B2 | 11/2014 | Fautz |
| 8,994,372 | B2 | 3/2015 | Bitz et al. |
| 9,018,951 | B2 | 4/2015 | Lai et al. |
| 9,035,653 | B2 | 5/2015 | Hutter et al. |
| 9,069,998 | B2 | 6/2015 | Bulumulla et al. |
| 9,086,446 | B2 | 7/2015 | Schulte |
| 9,229,074 | B2 | 1/2016 | Voigt et al. |
| 9,274,197 | B2 | 3/2016 | Wang et al. |
| 9,279,873 | B2 | 3/2016 | Xue et al. |
| 9,297,873 | B2 | 3/2016 | Block et al. |
| 9,307,925 | B2 | 4/2016 | Russell et al. |
| 9,389,293 | B2 | 7/2016 | Stemmer |
| 9,417,305 | B2 | 8/2016 | Zhai |
| 9,478,051 | B2 | 10/2016 | Li et al. |
| 2006/0253015 | A1* | 11/2006 | Nezafat ............ G01R 33/5635 600/410 |
| 2008/0024132 | A1 | 1/2008 | Brau et al. |
| 2010/0239151 | A1* | 9/2010 | Dannels ............ G01R 33/243 382/131 |
| 2010/0253336 | A1 | 10/2010 | Schneider et al. |
| 2010/0286500 | A1 | 11/2010 | Ruhm |
| 2011/0025327 | A1 | 2/2011 | Deoni et al. |
| 2011/0026799 | A1 | 2/2011 | Nehrke et al. |
| 2012/0002858 | A1* | 1/2012 | Huang ............ G01R 33/5611 382/131 |
| 2012/0007600 | A1 | 1/2012 | Boernert et al. |
| 2012/0150458 | A1 | 6/2012 | Sodickson et al. |
| 2012/0280683 | A1 | 11/2012 | Sacolick et al. |
| 2012/0306493 | A1 | 12/2012 | Voigt et al. |
| 2012/0306499 | A1 | 12/2012 | Hamamura et al. |
| 2013/0134972 | A1* | 5/2013 | Schulte ............ G01R 33/246 324/309 |
| 2013/0251227 | A1 | 9/2013 | Wang et al. |
| 2014/0056496 | A1 | 2/2014 | Kwak et al. |
| 2014/0103925 | A1 | 4/2014 | Hancu et al. |
| 2014/0152308 | A1 | 6/2014 | Lee et al. |
| 2014/0300354 | A1 | 10/2014 | He et al. |
| 2014/0340083 | A1 | 11/2014 | Zhang et al. |
| 2016/0054262 | A1 | 2/2016 | Sodickson et al. |
| 2016/0061921 | A1 | 3/2016 | Katscher et al. |

FOREIGN PATENT DOCUMENTS

| | | |
|---|---|---|
| WO | 2009118702 | 10/2009 |
| WO | 2010032172 | 3/2010 |
| WO | 2012054329 | 4/2012 |
| WO | 2012140536 | 10/2012 |
| WO | 2615470 | 7/2013 |
| WO | 2015158625 | 10/2015 |

OTHER PUBLICATIONS

Benkhedah, et al., Evaluation of adaptive combination of 30-channel head receive coil array data in 23Na MR imaging. Magn Reson Med. 2016;75(2):527-36.
Beqiri, et al., Comparison between simulated decoupling regimes for specific absorption rate prediction in parallel transmit MRI. Magn Reson Med. 2015;74(5):1423-34.
Blaimer, et al., Comparison of phase-constrained parallel MRI approaches: Analogies and differences. Magnetic Resonance in Medicine. 2016;75(3):1086-99.
Brunner, et al., SVD analysis of Array transmission and reception and its use for bootstrapping calibration. Magnetic resonance in medicine 76.6 (2016): 1730-1740.
Caeiros, et al., A new image reconstruction algorithm for real-time monitoring of conductivity and permeability changes in Magnetic Induction Tomography. Conference proceedings: Annual International Conference of the IEEE Engineering in Medicine and Biology Society IEEE Engineering in Medicine and Biology Society Conference. 2012; 2012:6239-42.
Collins, Recent and ongoing developments. Electromagnetics in Magnetic Resonance Imaging: Morgan & Claypool Publishers; 2016. p. 6-1-6-.
Degirmenci, et al., Image reconstruction in magnetic resonance conductivity tensor imaging (MRCTI). IEEE Trans Med Imaging. 2012;31(3):525-32.
Doneva, et al., Automatic coil selection for channel reduction in SENSE-based parallel imaging. Magma (New York, NY). 2008;21(3):187-96.
Hoffmann, et al., Numerical and experimental evaluation of RF shimming in the human brain at 9.4 T using a dual-row transmit array. Magnetic Resonance Materials in Physics, Biology and Medicine. 2014;27(5):373-86.
Katscher, et al., Determination of Electric Conductivity and Local SAR Via B1 Mapping. IEEE transactions on medical imaging. 2009;28(9):1365-74.
Liu, et al., Inter-echo variance as a weighting factor for multi-channel combination in multi-echo acquisition for local frequency shift mapping. Magn Reson Med. 2015;73(4):1654-61.
Ma, et al., Improved adaptive reconstruction of multichannel MR images. Medical physics. 2015;42(2):637-44.
Roemer, et al., The NMR phased array. Magn Reson Med. 1990;16(2):192-225.
Sbrizzi, et al., RF peak power reduction in CAIPIRINHA excitation by interslice phase optimization. NMR in Biomedicine. 2015;28(11):1393-401.
Schmid, et al., Dielectric properties of human brain tissue measured less than 10 h postmortem at frequencies from 800 to 2450 MHz.Bioelectromagnetics. 2003;24(6):423-30.
Schmidt, et al., A new approach for electrical properties estimation using a global integral equation and improvements using high permittivity materials. Journal of Magnetic Resonance. 2016;262:8-14.
Shin, et al. Initial study on in vivo conductivity mapping of breast cancer using MRI. Journal of magnetic resonance imaging 2015;42(2):371-8.

(56) References Cited

OTHER PUBLICATIONS

Ueno S. Studies on magnetism and bioelectromagnetics for 45 years: From magnetic analog memory to human brain stimulation and imaging. Bioelectromagnetics. 2012;33(1):3-22.
Vegh V, et al., Selective channel combination of MRI signal phase. Magn Reson Med. 2016; 76:1469-1477.
Wang, et al., T1 measurements incorporating flip angle calibration and correction in vivo. J Magn Reson. 2006;182(2):283-92.
Abdoli, et al., (2016) Phased-array combination for MR spectroscopic imaging using a water reference. Magn Reson Med.. 2016;76(3):733-41.
Allen, et al. (2011) Phase-sensitive sodium B1 mapping. Magn Reson Med 65(4):1125-1130.
Ammari, et al., (2015) Magnetic resonance-based reconstruction method of conductivity and permittivity distributions at the Larmor frequency. Inverse Problems. 31(10):105001.
Balezeau, et al., (2011) Mapping of low flip angles in magnetic resonance. Physics in medicine and biology 56(20):6635-6647.
Beatty, et al. Design of k-space channel combination kernels and integration with parallel imaging. Magn Reson Med. 2014;71(6):2139-54.
Bhakta, et al., (2008) Principles of electroanatomic mapping. Indian pacing and electrophysiology journal 8(1):32-50.
Boulant et al., High tip angle approximation based on a modified Bloch-Riccati equation, Magn Reson Med 2012; 67(2):339-43.
Breuer, et al., Dynamic autocalibrated parallel imaging using temporal GRAPPA (TGRAPPA). Magn Reson Med. 2005;53(4):981-5.
Brunner, et al., (2009) B1(+) interferometry for the calibration of RF transmitter arrays. Magn Reson Med 61(6):1480-1488.
By, Samantha, et al. "A 16-channel receive, forced current excitation dual-transmit coil for breast imaging at 7T." PloS one 9.11 (2014): e113969. http://journals.plos.org/plosone/article?id=info:doi/10.1371/journal.pone.0113969.
Bydder M, Larkman DJ, Hajnal JV. Combination of signals from array coils using image-based estimation of coil sensitivity profiles. Magn Reson Med. 2002;47(3):539-48.
Chang, (2012) Rapid B1 mapping using orthogonal, equal-amplitude radio-frequency pulses. Magn Reson Med 67(3):718-723.
Chung, et al., (2010) Rapid B1+ mapping using a preconditioning RF pulse with TurboFLASH readout. Magn Reson Med 64(2):439-446.
Cohen, Magnetoencephalography: evidence of magnetic fields produced by alpha-rhythm currents. Science 161.3843 (1968): 784-786.
Dowell, et al., (2007) Fast, accurate, and precise mapping of the RF field in vivo using the 180 degrees signal null. Magn Reson Med 58(3):622-630.
Eggenschwiler, et al., (2012) SA2RAGE: a new sequence for fast B1+− mapping. Magn Reson Med 67(6):1609-1619.
Hancu, et al., On conductivity, permittivity, apparent diffusion coefficient, and their usefulness as cancer markers at MRI frequencies. Magn Reson Med. 2015;73(5):2025-9.
Hansen, et al., Image reconstruction: An overview for clinicians. Journal of Magnetic Resonance Imaging. 2015;41(3):573-85.
Insko, et al., (1993) Mapping the radiofrequency field. J. Magn. Reson. Ser. A, (103):82-85.
Jin Keun Seo, et al., Electrical tissue property imaging using MRI at dc and Larmor frequency. Inverse Problems. 2012;28, 084002.
Jiru, et al., (2006) Fast 3D radiofrequency field mapping using echo-planar imaging. Magn Reson Med 56(6):1375-1379.
Jordanova, et al., (2014) B1 estimation using adiabatic refocusing: BEAR. Magn Reson Med 72(5):1302-1310.
Kamilov, et al., Isotropic inverse-problem approach for two-dimensional phase unwrapping. JOSA A. 2015;32(6):1092-100.
Kang, et al., (2013) Fast B1 mapping based on interleaved-three-flip-angle (ITFA) excitation. Medical physics 40(11):112301.
Katscher, et al., B(1)-based specific energy absorption rate determination for nonquadrature radiofrequency excitation. Magn Reson Med. 2012: 68:1911-18.

Katscher, et al., Recent progress and future challenges in MR electric properties tomography. Computational and mathematical methods in medicine. 2013;2013:546562.
Keil, et al., Massively parallel MRI detector arrays. Journal of Magnetic Resonance. 2013;229:75-89.
Khalighi, et al., (2012) RF pulse optimization for Bloch-Siegert B+1 mapping. Magn Reson Med 68(3):857-862.
Kim, et al., LORAKS makes better SENSE: Phase-constrained partial fourier SSENSE reconstruction without phase calibration. Magnetic resonance in medicine 77.3 (2017): 1021-1035.
Kimura, et al., Inhomogeneous noise correction combined with uniform filter and sensitivity map (INCUS) for multi-coil imaging including parallel imaging. Magn Reson Med. 2013;12(1):21-30.
Lee S-K, et al., Tissue electrical property mapping from zero echo-time magnetic resonance imaging. IEEE transactions on medical imaging. 2015;34(2):541-50.
Leitao, et al., "Absolute phase image reconstruction: a stochastic nonlinear filtering approach." IEEE Transactions on Image Processing 7.6 (1998): 868-882.
Lew, et al., SENSE phase-constrained magnitude reconstruction with iterative phase refinement. Magn Reson Med. 2007;58(5):910-21.
Li, et al., susceptibility mapping of human brain reflects spatial variation in tissue composition. Neuroimage. 2011;55(4):1645-56.
Lukzen et al., Analytical derivation of multiple spin echo amplitudes with arbitrary refocusing angle, J Magn Reson 2007, 185(1):71-6.
Lustig, et al., SPIRiT: Iterative self-consistent parallel imaging reconstruction from arbitrary k-space. Magn Reson Med. 2010;64(2):457-71.
Lutti A, et al. (2012) Robust and fast whole brain mapping of the RF transmit field B1 at 7T. PloS one 7(3):e32379.
Lyu, et al., Fast GRAPPA reconstruction with random projection. Magn Reson Med. 2015;74(1):71-80.
Marques, et al., Single acquisition electrical property mapping based on relative coil sensitivities: a proof-of-concept demonstration. Magn Reson Med. 2015;74(1):185-95.
Morrell, (2008) A phase-sensitive method of flip angle mapping. Magn Reson Med 60(4):889-894.
Morrell, et al., (2010) An analysis of the accuracy of magnetic resonance flip angle measurement methods. Physics in medicine and biology 55(20):6157-6174.
Murase et al., Numerical solutions to the time-dependent Bloch equations revisited, Magn Reson Imaging 2011; 29(1):126-31.
Nehrke, et al., (2012) DREAM—A novel approach for robust, ultrafast, multislice B(1) mapping. Magn Reson Med 68(5):1517-1526.
Nehrke, et al., (2014) Volumetric B1+ Mapping of the Brain at 7T using DREAM. Magnetic Resonance in Medicine, 71, 246-256.
Oran, et al., Feasibility of conductivity imaging using subject eddy currents induced by switching of MRI gradients. Magnetic resonance in medicine 77.5 (2017): 1926-1937.
Padormo, et al., Parallel transmission for ultrahigh-field imaging. NMR in Biomedicine. 2016;29(9):1145-61.
Park, et al., (2013) A statistical analysis of the Bloch-Siegert B1 mapping technique. Physics in medicine and biology 58(16):5673-5691.
Parker, et al., Phase reconstruction from multiple coil data using a virtual reference coil. Magn Reson Med. 2014;72(2):563-9.
Peng, et al. Optimized parallel imaging for dynamic PC-MRI with multidirectional velocity encoding. Magn Reson Med. 2010;64(2):472-80.
Perman, (1989) A method for correctly setting the rf flip angle. Magn Reson Med 9(1):16-24.
Rivoire, et al. (2011) Flip-angle measurement by magnetization inversion: Calibration of magnetization nutation angle in hyperpolarized (3) He magnetic resonance imaging lung experiments. Magn Reson Med 65(2):399-408.
Robinson, et al. An illustrated comparison of processing methods for MR phase imaging and QSM: combining array coil signals and phase unwrapping. NMR in Biomedicine 30.4 (2017): e3601.

(56) References Cited

OTHER PUBLICATIONS

Robinson, et al. Combining phase images from array coils using a short echo time reference scan (COMPOSER). Magnetic resonance in medicine 77.1 (2017): 318-327.
Rodgers, et al., Coil combination for receive array spectroscopy: Are data-driven methods superior to methods using computed field maps? Magn Reson Med. 2016;75(2):473-87.
Ropella, et al., A regularized, model-based approach to phase-based conductivity mapping using MRI. Magnetic resonance in medicine 78.5 (2017): 2011-2021.
Sacolick, et a., (2011) Fast radiofrequency flip angle calibration by Bloch-Siegert shift. Magn Reson Med 66(5):1333-1338.
Sacolick, et al., (2010) B1 mapping by Bloch-Siegert shift. Magn Reson Med 63(5):1315-1322.
Saranathan, et al., (2013) Efficient bloch-siegert B1+ mapping using spiral and echo-planar readouts. Magnetic Resonance in Medicine 70(6):1669-1673.
Sbrizzi, et al., (2014) Robust reconstruction of B 1+ maps by projection into a spherical functions space. Magnetic Resonance in Medicine, 71, 394-401.
Schar, et al., (2010) Simultaneous B(0)- and B(1)+-map acquisition for fast localized shim, frequency, and RF power determination in the heart at 3 T. Magn Reson Med 63(2):419-426.
Schulte, et al., (2011) Transmit gain calibration for nonproton MR using the Bloch-Siegert shift. NMR Biomed 24(9):1068-1072.
Sersa I. Enhanced sensitivity current density imaging. J Magn Reson. 2010;204(2):219-24.
Sigfridsson, et al., In vivo SNR in Dense MRI; temporal and regional effects of field strength, receiver coil sensitivity and flip angle strategies. Magnetic resonance imaging. 2011;29(2):202-8.
Sotiropoulos, et al., Effects of image reconstruction on fiber orientation mapping from multichannel diffusion MRI: reducing the noise floor using SENSE. Magn Reson Med. 2013;70(6):1682-9.
Stollberger, et al., (1996) Imaging of the active B1 field in vivo. Magn Reson Med 35(2):246-251.
Sung, et al., (2008) B1+ compensation in 3T cardiac imaging using short 2DRF pulses. Magn Reson Med 59(3):441-446.
Sung, et al., (2013) Simultaneous T(1) and B(1) (+) mapping using reference region variable flip angle imaging. Magn Reson Med 70(4):954-961.
Tse, et al., (2014) Encoding methods for B1(+) mapping in parallel transmit systems at ultra-high field. Journal of magnetic resonance (San Diego, Calif.: 997) 245:125-132.
Uecker, et al., ESPIRiT—an eigenvalue approach to autocalibrating parallel MRI: Where SENSE meets GRAPPA. Magn Reson Med. 2014;71(3):990-1001.
Uecker, et al., Estimating absolute-phase maps using ESPIRiT and virtual conjugate coils. Magnetic resonance in medicine77.3 (2017): 1201-1207.
Van Lier, et al. B 1+ Phase mapping at 7 T and its application for in vivo electrical conductivity mapping. Magn Reson Med. 2012;67(2):552-61.
Van Lier, et al., Electrical properties tomography in the human brain at 1.5, 3, and 7T: a comparison study. Magnetic resonance in medicine 71.1 (2014): 354-363.
Vashaee, et al., (2013) B1 mapping with a pure phase encode approach: quantitative density profiling. Journal of magnetic resonance (San Diego, Calif.: 1997) 232:68-75.
Voigt, et al., Quantitative conductivity and permittivity imaging of the human brain using electric properties tomography. Magn Reson Med. 2011;66(2):456-66.
Wan Y, Negishi M, Constable RT. A feasibility study of magnetic resonance driven electrical impedance tomography using a phantom. Physiological measurement. 2013;34(6):623.
Wang, et al., (2006) T1 measurements incorporating flip angle calibration and correction in vivo. Journal of magnetic resonance (San Diego, Calif.: 1997) 182(2):283-292.
Wang, et al., (2009) Rapid 3D radiofrequency field mapping using catalyzed double-angle method. NMR Biomed 22(8):882-890.
Wang, et al., A new method to derive white matter conductivity from diffusion tensor MRI. IEEE Trans Biomed Eng. 2008;55(10):2481-6.
Wang, et al., Constable RT. Measurement and correction of transmitter and receiver induced nonuniformities in vivo. Magn Reson Med. 2005;53(2):408-17.
Wang, et al., In vivo method for correcting transmit/receive nonuniformities with phased array coils. Magn Reson Med. 2005;53(3):666-74.
Weis, et al., (2005) A simple method for mapping the B1 field distribution of linear RF coils. Magma 18(6):283-287.
Yamaguchi-Sekino, et al., Biological effects of electromagnetic fields and recently updated safety guidelines for strong static magnetic fields. Magn Reson Med. 2011;10(1):1-10.
Yarnykh, (2007) Actual flip-angle imaging in the pulsed steady state: a method for rapid three-dimensional mapping of the transmitted radiofrequency field. Magn Reson Med 57(1):192-200.
Zhang, et al., Complex B1 mapping and electrical properties imaging of the human brain using a 16-channel transceiver coil at 7T. Magn Reson Med. 2013;69(5):1285-96.
Zhang, et al., Imaging electric properties of biological tissues by RF field mapping in MRI. IEEE Trans Med Imaging. 2010;29(2):474-81.
Zhang, et al., Magnetic-resonance-based electrical properties tomography: a review. IEEE reviews in biomedical engineering. 2014;7:87-96.
Zhou, et al. "Amide proton transfer (APT) contrast for imaging of brain tumors." Magnetic Resonance in Medicine: An Official Journal of the International Society for Magnetic Resonance in Medicine 50.6 (2003): 1120-1126.
International Search Report and Written Opinion of the International Searching Authority, Application No. PCT/US2016/032671, dated Aug. 18, 2016, 12 pages.
Cunningham, et al., (2006) Saturated double-angle method for rapid B1+ mapping. Magn Reson Med 55(6):1326-1333.
Dagher, et al., MAGPI: A framework for maximum likelihood MR phase imaging using multiple receive coils. Magnetic Resonance in Medicine. 2016;75(3):1218-31.
Damijan, et al., Electric properties of tissues. Encyclopedia of biomedical engineering, 2006:12 pages.
Dowell, et at, (2007) Fast, accurate, and precise mapping of the RF field in vivo using the 180 degrees signal null. Magn Reson Med 58(3):622-630.
Duan, et al., (2013) Improved Bloch-Siegert based B1 mapping by reducing off-resonance shift. NMR Biomed 26(9):1070-1078.
Duyn, et al., High-field MRI of brain cortical substructure based on signal phase. Proceedings of the National Academy of Sciences. 2007;104(28):11796-801.
Duyn, et al., Simple correction method fork-space trajectory deviations in MRI. Journal of Magnetic Resonance. 1998;132(1):150-3.
Eggenschwiler, et at, (2012) SA2RAGE: a new sequence for fast B1+-mapping. Magn Reson Med 67(6):1609-1619.
Feng L, et al. Golden-angle radial sparse parallel MRI: combination of compressed sensing, parallel imaging, and golden-angle radial sampling for fast and flexible dynamic volumetric MRI. Magn Reson Med. 2014;72(3):707-17.
Ferrand, et al., (2014) Accelerating parallel transmit array B1 mapping in high field MRI with slice undersampling and interpolation by kriging. IEEE transactions on medical imaging 33(8):1726-1734.
Gol, et al., A subspace-based coil combination method for phased-array magnetic resonance imaging. Magn Reson Med. 2016;75(2):762-74.
González, et al., Robust phase unwrapping by convex optimization. 2014 IEEE International Conference on Image Processing (ICIP); 2014: IEEE, 6 pages.
Griswold, et al. Generalized autocalibrating partially parallel acquisitions (GRAPPA). Magn Reson Med. 2002;47(6):1202-10.

* cited by examiner

SYSTEMS AND METHODS FOR ESTIMATING COMPLEX B1+ FIELDS OF TRANSMIT COILS OF A MAGNETIC RESONANCE IMAGING (MRI) SYSTEM

CROSS-REFERENCE TO RELATED APPLICATIONS

This application is a national stage application filed under 35 U.S.C. 071 of PCT/US2016/032671 filed on May 16, 2016, which claims the benefit of U.S. Provisional Patent Application No. 62/161,569, filed on May 14, 2015, entitled "SYSTEMS AND METHODS FOR ESTIMATING B1 FIELDS OF TRANSMIT AND RECEIVE COILS OF A MAGNETIC RESONANCE IMAGING (MRI) SYSTEM," the disclosures of which are expressly incorporated herein by reference in their entireties.

BACKGROUND

Magnetic resonance imaging (MRI) is one of the most important modern medical imaging modalities. It has far less risk of side effects than most other imaging modalities such as radioscopy with x-rays or computed tomography because patient and medical personal are not subjected to ionizing radiation exposure in the procedure. The use of MRI has grown very fast. Every year, more than 30 million MRI scans are performed in the United States; more than 60 million MRI scans are performed worldwide. Doctors often recommend MRI for the diagnoses of various diseases, such as tumors, strokes, heart problems, and spine disease. A high-quality scan is important for maximizing diagnostic sensitivity and making the right diagnosis. Generally, a high quality image requires high signal to noise ratio (SNR), high contrast between normal and pathological tissues, low levels of artifact, and reasonable and acceptable spatial-temporal resolution.

In order to obtain a detectable nuclear magnetic resonance (NMR) or magnetic resonance imaging (MRI) or magnetic resonance (MR) signal, the object being imaged (also referred to herein as "object" or "subject") must be exposed to a static basic magnetic field (usually designated as the $B_0$ field) which is as homogeneous as possible. The basic magnetic field can be generated by a basic field magnet of the MRI system. While the magnetic resonance images are being recorded, the basic magnetic field has fast-switched gradient fields superimposed on it for spatial encoding, which are generated by gradient coils. Moreover, using radio-frequency (RF) antennas, radio-frequency pulses with a defined field strength are radiated into the objected being imaged. RF field of these RF pulses is normally designated as $B_1^+$. Using these RF pulses, the nuclear spins of the atoms in the object being imaged are excited such that the atoms are deflected by a so-called "excitation flip angle" ($\alpha$) from their equilibrium position parallel to the basic magnetic field $B_0$. The nuclear spins then process around the direction of the basic magnetic field $B_0$. The magnetic resonance signals generated in this manner are recorded by RF receiver coil. The receiver coil can be either the same coil which was used to generate the RF pulses (i.e., a transceiver coil) or a separate receive-only coil.

The magnetic resonance images of the object are generated based on the received magnetic resonance signals. The MR signal is picked up by a receive coil, amplified and processed. The acquired measurements are digitized and stored as complex numerical values in a "k-space" matrix. An associated MR image can be reconstructed from the k-space data, for example, by an inverse 2D or 3D fast Fourier transform (FFT) from raw data, which are collected in the spatial frequency domain (the "k-space"). The k-space data includes multiple lines acquired with different phase encoding. Each line is digitized by collecting a number of samples. A set of k-space data is converted to a MR image by means of Fourier transformation. Each image point in the magnetic resonance image is assigned to a small body volume known as a "voxel" and each brightness or intensity value of the images points is linked to the signal amplitude of the magnetic resonance signal received from this voxel. The relationship between the resonantly radiated $B_1^+$ and the flip angle $\alpha(x)$ is assumed by the following equation:

$$\alpha(x) = 2\pi\gamma B_1^+(x) \int_0^T f(t)dt \quad (1)$$

where $\gamma$ is the gyromagnetic ratio, which can be considered to be a fixed material constant for most nuclear spin studies, and $\tau$ is the influence duration of the radio-frequency pulse. $f(t)$ is the time dependent transmitter voltage defining the RF pulse shape. Eq. (1) holds true if the frequency of the RF pulse equals the Larmor-frequency of the magnetization.

Before the commencement of each NMR or MRI scan, it is common practice to adjust the strength of the transmit field and/or the receiver sensitivity to ensure that the RF excitation pulses have the optimal frequency, strength and duration to evoke the desired NMR or MRI or MR signal. This does not necessarily mean that the expected RF transmit field will be produced uniformly throughout a cross section and/or a volume of the object being imaged, or that the resulting NMR or MRI or MR signals will be received uniformly from all locations. Transmit RF field produced by most transmit coils as loaded by the object being imaged is not homogeneous, and the receive field of most receive coils is similarly not homogeneous. This is particularly true of imperfect coil configuration, such as surface coil and phase array coils. Even if the transmit and receive coil fields are homogeneous for free space (i.e., the unloaded space or space in the absence of the object), wave behavior and penetration of the RF field into the subject may give rise to non-uniform transmit field and receiver sensitivity throughout the region of interest. This is known as the subject loading effect, and this effect becomes pronounced at higher static $B_0$ magnetic fields such as at static magnetic field of about 3 Tesla or higher. Even at lower static magnetic fields, the subject loading effect may be non-negligible. Moreover, the incorrect calibration of the RF pulse amplitude, instability or drift of the RF amplifier or other RF electronics, can lead to non-uniform transmit field. Also, mutual inductance between the transmit and receive coils may cause further inhomogeneities in the transmit and receive fields.

SUMMARY

Described herein are systems and methods for quickly, accurately and robustly estimating transmit field of an RF transmit coil ($B_1^+$) of an MRI scanner system in the k-space domain. For example, the systems and methods described herein relate to techniques for estimating complex transmit field $B_1^+$ of a transmit coil or coil element of a transmit coil array. As compared to conventional techniques for estimating $B_1^+$ using magnitude or phase images in the image domain, the techniques described herein using k-space lines from one or more images can greatly reduce the time required to, as well as improve the accuracy of, $B_1^+$ mapping. It should be understood that the techniques described herein can be applied in a wide range of applications including, but not limited to, RF coil design, RF shimming, image quality improvement, complex scanner design, electromagnetic property tomography imaging with MRI, and quantitative MRI (e.g., $T_1$ and perfusion imaging).

An example method of estimating transmit field $B_1^+$ in the k-space domain is described herein that includes: (1) encoding both $B_1$ phase and $B_1$ magnitude in the acquisition sequence; (2.) acquiring 2 dimensional (2D) or 3 dimensional (3D) full k-space data and/or sub-set k-space data (e.g., partial k-space data) with different imaging parameters and/or receiver coil; (3) applying an algorithm to the k-space data for estimating a complex $B_1^+$ map; and (4) storing the complex $B_1^+$ map for use with clinical and research applications.

In some implementations, as described below, the techniques for estimating the complex $B_1^+$ map in the k-space domain can be used for estimating the transmit field $B_1^+$ of a refocusing RF pulse field, a magnetization preparation RF pulse field, and/or selective RF pulse field.

Another method for estimating transmit field $B_1^+$ in the image domain is described herein that includes: (1) encoding both $B_1$ phase and $B_1$ magnitude in the acquisition sequences; (2) acquiring 2 dimensional (2D) or 3 dimensional (3D) full k-space data with different imaging parameters; (3) applying FFT transform to the full k-space data for obtaining images; (4) using the images for estimating the complex $B_1^+$ map; and (5) storing the complex $B_1^+$ map for use in clinical and research applications.

In some implementations, as described below, a complex $B_1^+$ map is applied in $B_1^+$ inhomogeneity correction, RF safety evaluation, RF transmit coil design evaluation and optimization, quantitative MRI and MRS, electromagnetic property tomography, MRI quality control, RF shimming, tailored RF shimming, and/or parallel transmit field.

An example method for determining spatial distribution of magnitude and phase of radio frequency (RF) transmit field $B_1^+$ in a magnetic resonance imaging (MRI) system is described herein. The method can include applying at least one pulse sequence configured to excite precessing nuclear spins in magnetic resonance (MR) nuclei. The at least one pulse sequence can include at least one RF pulse having encoded $B_1$ phase and encoded $B_1$ magnitude. The method can also include detecting a plurality of MR signals representing nuclear MR signals arising from the precessing nuclear spins in the MR nuclei, acquiring at least two sets of complex k-space data including an RF pulse having encoded $B_1$ phase from the MR signals, and acquiring at least two sets of complex k-space data including an RF pulse having encoded $B_1$ magnitude from the MR signals. The method can further include estimating a complex $B_1^+$ map of at least a portion of a transmit coil of the MRI system using the acquired sets of complex k-space data.

As used herein, the complex k-space data can optionally be a complex k-space image. Additionally, each set of complex k-space data including an RF pulse having encoded $B_1$ phase can have a different encoded $B_1$ phase. For example, each set of complex k-space data can be a complex k-space image with different encoded $B_1$ phase, i.e., at least two complex k-space images, each complex k-space image including an RF pulse having a different encoded $B_1$ phase as compared to the other complex k-space image. Additionally, each set of complex k-space data including an RF pulse having encoded $B_1$ magnitude can have a different encoded $B_1$ magnitude. For example, each set of complex k-space data can be a complex k-space image with different encoded $B_1$ magnitude, i.e., at least two complex k-space images, each complex k-space image including an RF pulse having a different encoded $B_1$ magnitude as compared to the other complex k-space image.

Optionally, in some implementations, the method can include applying a plurality of pulse sequences, where a first pulse sequence comprises at least one RF pulse having encoded $B_1$ phase and a second pulse sequence comprises at least one RF pulse having encoded $B_1$ magnitude. Alternatively or additionally, the at least one RF pulse can be a single RF pulse. In other words, a single RF pulse can have both encoded $B_1$ phase and encoded $B_1$ magnitude. Alternatively or additionally, the at least one RF pulse can optionally be a plurality of RF pulses. Optionally, the RF pulses can include at least one RF pulse having encoded $B_1$ phase and at least one RF pulse having encoded $B_1$ magnitude. The RF pulse having encoded $B_1$ phase and the RF pulse having encoded $B_1$ magnitude can be the same or different RF pulses. This disclosure contemplates that a plurality of phase and magnitude encoded RF pulses can combine with themselves (and optionally other RF pulses) to create a pulse sequence for image acquisition.

Alternatively or additionally, the at least two sets of complex k-space data including at least an RF pulse having encoded $B_1$ phase can include full k-space or a portion of k-space, Alternatively or additionally, the at least two sets of complex k-space data including at least an RF pulse having encoded $B_1$ magnitude can include full k-space or a portion of k-space.

Alternatively or additionally, the at least one RF pulse can be on-resonance excitation. Alternatively or additionally, the at least one RF pulse can be off-resonance excitation.

Alternatively or additionally, the at least one RF pulse can be a rectangle RF pulse, a truncated-sinc RF pulse, a sinc RF pulse, a Gaussian RF pulse, an adiabatic RF pulse, a Hermite RF pulse, a Shinnar-Le Roux RF pulse, or combinations thereof.

Alternatively or additionally, the complex $B_1^+$ map can be estimated using data in a k-space domain.

Alternatively or additionally, the method can optionally further include transforming each of the at least two sets of complex k-space data including an RF pulse having encoded $B_1$ phase into a respective image in an image domain, and transforming each of the at least two sets of complex k-space data including an RF pulse having encoded $B_1$ magnitude into a respective image in the image domain. This disclosure contemplates that the complex k-space data can be transformed into the image domain using an inverse Fourier transform such as an inverse 2D or 3D FFT, for example. Additionally, the complex $B_1^+$ map of at least the portion of the transmit coil of the MRI system can be estimated based on the respective images. In other words, the complex $B_1^+$ map can be estimated in the image domain. For example, estimating the complex $B_1^+$ map based on the respective images can include using at least one a double flip angle method, a dual pulse spin echo method, an actual flip angle imaging method, a steady state method, a dual refocusing echo acquisition mode (DREAM) method, a Bloch Siegert shift method, or a phase sensitive method. Alternatively or additionally, estimating the complex $B_1^+$ map based on the respective images can further include estimating the complex $B_1^+$ map based on a relationship between a complex MR signal and the respective images. For example, the complex $B_1^+$ map can be estimated using an analytic, empirical, or approximated solution of Bloch equations.

Alternatively or additionally, estimating the complex $B_1^+$ map of at least the portion of the transmit coil of the MRI system can further include estimating a k-space domain convolution kernel between k-space of the at least two sets of complex k-space data including an RF pulse having encoded $B_1$ phase and the at least two sets of complex k-space data including an RF pulse having encoded $B_1$ magnitude. In other words, the complex $B_1^+$ map can be estimated in the k-space domain. For example, the k-space domain convolution kernel can be estimated using a fitting algorithm. The complex $B_1^+$ map can then be transformed into an image domain using an inverse Fourier transform such as an inverse 2D or 3D FFT, for example.

Alternatively or additionally, the at least two sets of complex k-space data including an RF pulse having encoded $B_1$ phase or the at least two sets of complex k-space data including an RF pulse having encoded $B_1$ magnitude can be acquired using at least one of different MRI system configurations. For example, the different MRI system configurations include at least one of different coil elements of a receive coil, different receive coils, or different gradient encoding strategies. Alternatively or additionally, the at least two sets of complex k-space data including at least an RF pulse having encoded $B_1$ phase or the at least two sets of complex k-space data including at least an RF pulse having encoded $B_1$ magnitude can be acquired using different image contrasts.

Alternatively or additionally, the complex $B_1^+$ map can be applied for at least one type of RF pulse.

Alternatively or additionally, the method can optionally further include, using the complex $B_1^+$ map, generating a refocusing RF pulse, a selective RF pulse, or a magnetization preparation RF pulse.

Alternatively or additionally, the method can optionally further include applying the complex $B_1^+$ map to improve performance of simultaneous multi-slice excitation.

Alternatively or additionally, the method can optionally further include storing the complex $B_1^+$ map in a memory.

Alternatively or additionally, the MRI system can include a plurality of RF transmit channels or elements. Additionally, the at least two sets of complex k-space data including at least an RF pulse having encoded $B_1$ phase or the at least two sets of complex k-space data including at least an RF pulse having encoded $B_1$ magnitude can be acquired using an acquisition pulse sequence that is repeated a plurality of times using different ones or combinations of the RF transmit channels or elements for respectively corresponding different acquisition pulse sequences.

An example magnetic resonance imaging (MRI) system for determining spatial distribution of magnitude and phase of radio frequency (RF) transmit field $B_1^+$ is described herein. The MRI system can include a transmitting and receiving unit including at least one RF coil, and an MRI system controller operably coupled with the transmitting and receiving unit. The transmitting and receiving unit can be configured to apply at least one pulse sequence using the at least one RF coil. The at least one pulse sequence can be configured to excite precessing nuclear spins in magnetic resonance (MR) nuclei, and the at least one pulse sequence can include at least one RF pulse having encoded $B_1$ phase and encoded $B_1$ magnitude. The transmitting and receiving unit can also be configured to detect a plurality of MR signals using the at least one RF coil. The MR signal can represent nuclear MR signals arising from the precessing nuclear spins in the MR nuclei. The MRI system controller can include a processor and a memory, the memory having computer-executable instructions stored thereon that, when executed by the processor, cause the processor to acquire at least two sets of complex k-space data including an RF pulse having encoded $B_1$ phase from the MR signals, acquire at least two sets of complex k-space data including an RF pulse having encoded $B_1$ magnitude from the MR signals, and estimate a complex $B_1^+$ map of at least a portion of a transmit coil of the MRI system using the acquired sets of complex k-space data.

An example non-transitory computer-readable recording medium having computer-executable instructions stored thereon for determining spatial distribution of magnitude and phase of radio frequency (RF) transmit field $B_1^+$ is described herein. The computer-executable instructions, when executed by a processor, can cause the processor to receive a plurality of magnetic resonance (MR) signals representing nuclear MR signals arising from precessing nuclear spins in MR nuclei, acquire at least two sets of complex k-space data including an RF pulse having encoded $B_1$ phase from the MR signals, acquire at least two sets of complex k-space data including an RF pulse having encoded $B_1$ magnitude from the MR signals, and estimate a complex $B_1^+$ map of at least a portion of a transmit coil of the MRI system using the acquired sets of complex k-space data.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

As shown in FIG. 4, K-space data from multiple receive coils can be lumped together to estimate the $B_1^+$ mapping.

As shown in FIG. 5, the conventional double flip angle method does not have the phase of the $B_1^+$ mapping. In contrast, the $B_1^+$ mapping technique described herein has both phase and magnitude of the $B_1^+$ mapping.

As shown in FIG. 6, the conventional double flip angle method does not have the phase of the $B_1^+$ mapping.

Figure 1:
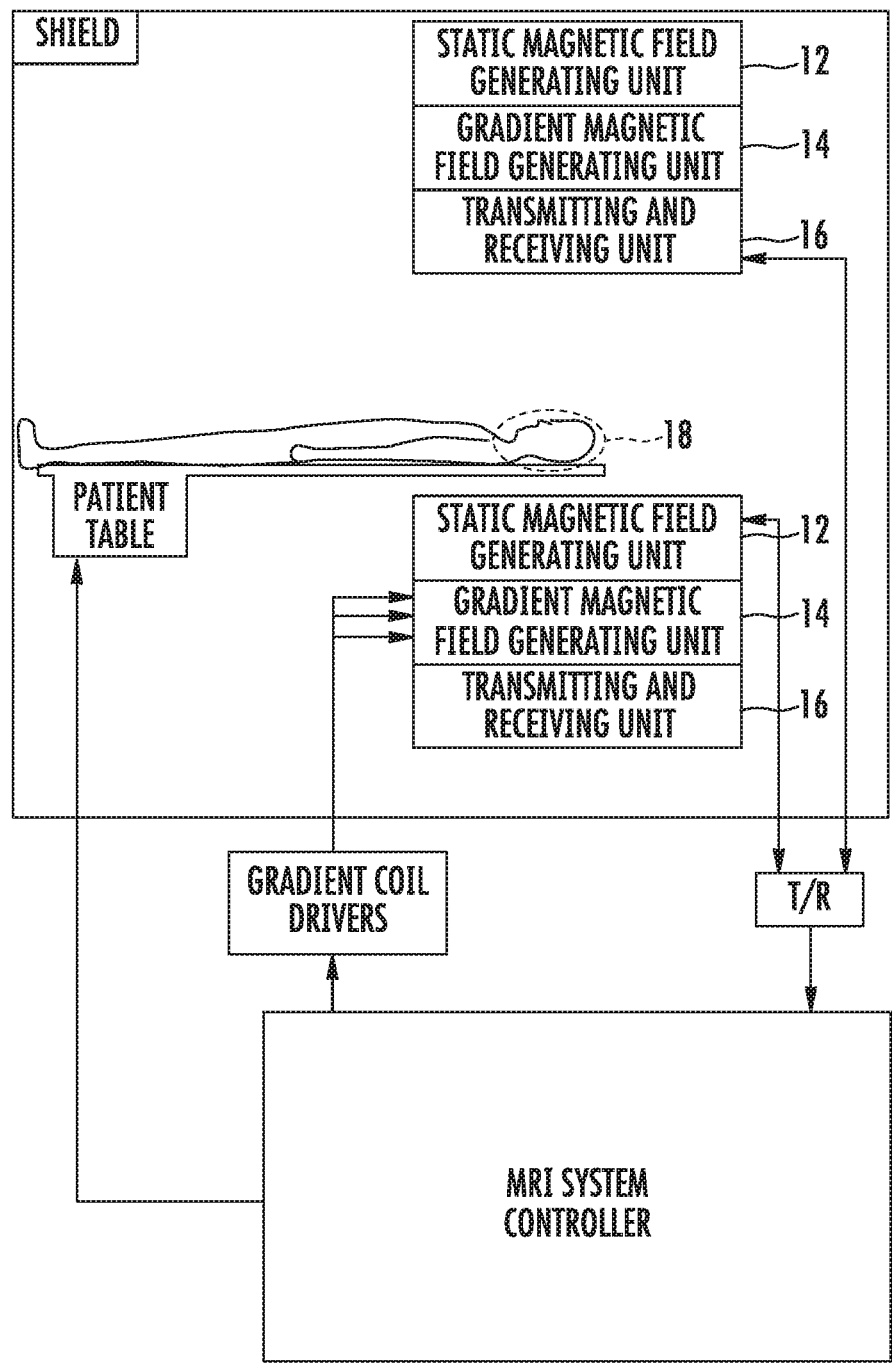
FIG. 1 is a schematic diagram illustrating an example MRI system.

In contrast, the $B_1^+$ mapping technique described herein has both phase and magnitude of the $B_1^+$ mapping.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not.

Definitions $B_1$ is the transmit RF field which is generated by a transmit coil in MRI system. $B_1$ includes a transversal transmit field $B_{xy}$ and a longitudinal transmit field $B_z$.

$B_1^+$ is the positive circularly polarized component of a transversal transmit field of a RF pulse which is generated by a transmit coil. The RF pulse can be used as an excitation RF pulse, refocused RF pulse, and magnetization preparation RF pulse. The transmit coil can be at least one of volume coil, surface coil, one element of an array coils, or a combination thereof. The transversal transmit RF field can be decomposed into two rotating fields: the positive circularly polarized component $B_1^+$, which rotates in the direction of nuclear magnetic moment precession (counterclockwise direction), and the negative circularly polarized component $B_1^-$, which rotates opposite to the direction of precession (clockwise direction). In an MRI system, only the positive circularly polarized component of the transmitting field $B_1^+$ contributes to the excitation of proton nuclei spins. Therefore, as used herein, $B_1^+$ refers to the transmit field of a transmit coil.

It should be understood that the MRI systems described herein can include a plurality of transmit coils and/or a plurality of receiver coils. Optionally, the transmit and/or receiver coils can be an array coil (e.g., transmit coil elements arranged in an array and/or receiver coil elements arranged in an array). In some implementations, the transmit and receiver coils are different coils. In other implementations, the transmit and receiver coil are the same coil (e.g., a transceiver coil). Alternatively or additionally, the transmit coil can include, but is not limited to, a transmit volume coil, a transmit surface coil, or an array coil. In some implementations, the complex $B_1^+$ map described herein can be a complex $B_1^+$ map of a portion of the transmit coil or element of an array coil. In some implementations, the complex $B_1^+$ map described herein can be a complex $B_1^+$ map of the entire transmit coil or element of an array coil.

As used herein, encoded RF pulse can refer to encoded excitation RF pulses and/or encoded reference RF pulses. The encoded excitation RF pulses are used as excitation RF pulses and estimation of complex $B_1^+$ mapping of the encoded excitation RF pulses. The encoded reference RF pulses are used as non-excitation RF pulses and estimation of complex $B_1^+$ mapping of the encoded non-excitation RF pulses. The encoded reference RF pulses include at least one of off-resonance RF pulse, saturation pulse, inversion recovery RF pulse, or other magnetization preparation pulse.

$B_1$ Mapping Overview $B_1^+$ field estimation is significant to applications including, but not limited to, image quality improvement, RF safety, RF coil design and optimization, quantitative MRI, RF shimming, tailored RF shimming, parallel transmit field, and electromagnetic property tomography.

Inhomogeneous transmit or inhomogeneous receiver sensitivity (or both) can give rise to signal and contrast inhomogeneities in the reconstructed images. Without removing or sufficiently reducing these $B_1$ inhomogeneities, the value of MRI images in clinic and research may be compromised.

$B_1^+$ estimation can also be important for RF safety in high field and ultra-high field MRI. $B_1$ inhomogeneities can generate a local exposure where most of the absorbed energy is applied to one body region rather than the entire body. As a result, the hotspots may occur in the exposed tissues and may lead to regional damage of these tissues even when global specific absorption rate (SAR) is less than U.S. Food and Drug Administration (FDA) and International Electrotechnical Commission (IEC) SAR limits.

$B_1^+$ field estimation can also be important for RF coil design. The uniformity of $B_1^+$ field is an important metric for RF coil design and optimization. The $B_1^+$ field estimation can be a direct and efficient method to evaluate the performance of RF coil. As for a RF coil design and validation, fast and accurate $B_1^+$ field estimation can improve the efficiency for RF coil design and evaluation. As for specific application RF coil, such as knee coil, breast coil, the RF inhomogeneity can be greatly improved if the loaded effect is taken account into the coil design.

Correction of $B_1^+$ inhomogeneity can also be important for quantitative MRI, such as quantitative fast $T_1$ mapping and MR image segmentation. It is known that contrast-to-noise ratio and signal inhomogeneity are major factors that strongly affect the performance of segmentation. In quantitative MRI, one solution is to measure an absolute $B_1^+$ and correct the intensity inhomogeneities that arise from $B_1^+$ variations.

$B_1^+$ can also provide information about coil performance and inhomogeneity and can also be used for preventive maintenance of RF system.

RF shimming, tailored RF shimming, and parallel transmission are techniques that enable high field and ultra-high field MRI at maximum image quality and RF patient safety. These techniques are based on accurate $B_1^+$ mapping and adjust current amplitude and phase of each element of the RF coils and/or gradient configuration to maximize $B_1^+$ or flip angle uniformity in subsequent imaging. The estimation of transmit field $B_1^+$ is a precondition of RF shimming and parallel transmission techniques. RF shimming technique is coil configuration and object dependent. Thus, the transmit field $B_1^+$ must be estimated for each coil and object when using the RF shimming technique. Reducing time for estimating transmit field $B_1^+$ reduces the time of applying RF shimming technique in clinical settings. Additionally, parallel transmission technique is coil configuration, object, and sequence dependent. Therefore, the transmit field $B_1^+$ must be estimated for each coil, object, and sequence when using the parallel transmit technique. Reducing time for estimating transmit field $B_1^+$ reduces the time of applying parallel transmit technique in clinical settings.

$B_1^+$ mapping has an increasing role in electrical property tomography. The conductivity and permittivity of living issues can be directly estimated using $B_1^+$ mapping.

More recently, it has become possible to omit the use of all conventional main field gradients using only RF encoding to achieve spatial resolution, alleviating problems that come along with switched gradients like acoustic noise. For example, single echo acquisition (SEA) imaging uses a one-dimensional array of long and narrow parallel elements to localize the image information in one direction, and an entire image is obtained from a single line of k-space, avoiding rapid or repeated manipulation of gradients.

MRI signals strongly relate to MRI tissue properties (such as $T_1$ and $T_2$ relaxation time), hardware configuration, sequence, RF pulse profile, and/or imaging parameters. Thus, an ideal $B_1$ mapping based on MRI techniques may have one or more of the following characteristics: MRI tissue properties independent; $B_0$ inhomogeneity and susceptibility independent; short scan time; large dynamic range; insensitive to imperfect spoiling or RF profile; insensitive to signal to noise (SNR); RF safety; and/or high accuracy and low precision of $B_1$ field estimation.

Recently, three major developments can be envisaged in MRI: the use of parallel acquisition methods, the move to high field, and the development of new MRI scanner designs such as open access scanners. For these developments, the inhomogeneous signal intensity from non-tissue characteristics (such as inhomogeneous transmission and reception) has been being a greater problem. Estimating transmit field is precondition of developing the techniques to correct the inhomogeneous signal intensity which is caused by the transmit field.

Estimating transmit field $B_1^+$ and its mapping have wide applications in MRI industry and clinical practice, including: adjusting voltage of an RF amplifier for desired flip angle; understanding or correcting signal and contrast inhomogeneity through tissue and space to improve diagnostic performance; improving the accuracy and precision of quantitative MRI, such as $T_1$, $T_2$ and MRS, segmentation; optimizing coil design; improving the performance of multiple transmit techniques (parallel transmit, RF shimming, pulse design); evaluating RF safety and MRI safety; and/or exploring new contrast, such as conductivity and permittivity contrast.

A number of techniques have been proposed for estimating transmit field in vivo in both image domain and k-space domain. In image domain, the techniques can be categorized into MR amplitude based methods and MR phase based methods. MR amplitude based methods include the double flip angle method [Insko E K et al, 1993; U.S. Pat. No. 7,446,526], dual pulse spin echo method [Jiru F et al, 2006], actual flip angle imaging method [Yarnykh V L, 2007], steady state method [Brunner et al, 2009], and composite pulses [Nehrke K et al. 2012; EP 2615470]. MR phase based methods include Bloch Siegert shift method [U.S. Pat. Nos. 8,198,891, 8,558,547, 9,086,446], phase sensitive method [U.S. Pat. No. 8,305,077], adiabatic pulses [U.S. Pat. No. 8,258,786; Jordanova K V, 2014], and other signal phase manipulation techniques [Chang Y V 2012]. Additionally, a method [U.S. Pat. No. 8,077,955] has been proposed to estimate spatial patterns and amplitudes of transmit RF fields in MRI systems using frequency filtering of spatially modulated or "tagged" MRI data in k-space domain.

All MR amplitude based methods in image domain [e.g., Insko E K et al, 1993; U.S. Pat. No. 7,446,526; Nehrke K et al. 2012; EP 2615470], only encode $B_1$ magnitude into excitation RF pulse and provide the magnitude of $B_1^+$. In other words, the MR amplitude based methods do not include encoding $B_1$ phase. For example, a double flip angle method encodes $B_2$ magnitude into two excitation RF pulses of flip angles of $\alpha$ and $2\alpha$. Because $2\alpha$ are realized by doubling magnitude of $B_1$ field, the phase of RF pulse at the flip angle of $\alpha$ is the same as that at the flip angle of $2\alpha$. The phase difference of $B_1^+$ is therefore not encoded into the two excitation RF pulses. As a result, only the magnitude (but not the phase) of transmit field $B_1^+$ can be estimated by the double flip angle method.

The MR phase based method [U.S. Pat. No. 8,305,077] applies a composite pulse to encode $B_1$ phase and estimates $B_1$ magnitude through computing a phase difference between the two phase measurements and generating a radio frequency magnitude map based on the phase difference. This method, however, does not provide a complex $B_1^+$ map, and instead only provides magnitude of transmit field $B_1^+$.

Bloch Siegert shift method [U.S. Pat. Nos. 8,198,891, 8,558,547, 9,086,446] encodes $B_1$ phase in at least one MR excitation pulse as an encoded $B_1$ phase MR excitation pulse and encodes $B_1$ magnitude in at least one off-resonance MR pulse as an encoded $B_1$ magnitude off-resonance MR excitation pulse. The applied far off-resonant RF pulses to a magnetization induce a Bloch Siegert phase shift in the transverse component. The magnitude of transmit field $B_1^+$ can be estimated by the Bloch Siegert phase shift. However, the Bloch Siegert shift method does not provide a complex $B_1^+$ map.

A recently proposed technique, i.e., "B1 estimation using adiabatic refocusing" (BEAR) method [Jordanova K V, 2014], uses adiabatic pulses to induce a spin-echo with phase that has a linear dependence on magnitude of $B_1^+$. That is, BEAR method encodes the magnitude of transmit field $B_1^+$ into successive refocusing pulses. As a result, the magnitude of transmit field $B_1^+$ can be estimated by the linear relationship between phase and $B_1$ field strength. However, the BEAR method does not provide a complex $B_1^+$ map.

In k-space domain, the magnitude of transmit $B_1^+$ is estimated using frequency filtering of spatially modulated or "tagged" MRI data in k-space domain [U.S. Pat. No. 8,077, 955]. The method requires at least one two-dimensional set of $B_1$ amplitude-tagged MRI data. The application of Tagged RF pulse (180) will increase SAR of patients and have a potential risk. Additionally, this method cannot provide the estimation of $B_1^+$ phase. In other words, the method does not provided a complex $B_1^+$ map.

As described above, existing techniques for transmit field $B_1^+$ focus on image domain and can be divided into signal intensity-sensitive methods (e.g., amplitude-based methods) and phase-sensitive methods (e.g., phase-based methods).

Among signal intensity-sensitive methods, there are a couple of double or multi-angle techniques. These methods use multiple (e.g., two) spin- or gradient-echo recalled acquisitions with different flip angles of the exciting RF pulses in the individual sub-experiments. By using the ratio of signal intensities, in case of two acquisitions, or fitting the signal behavior, the effective flip angle, which is proportional to the actual $B_1^+$ can be estimated. However, these methods are not efficient, because a long repetition time (TR) need to be used to achieve full relaxation so that the effect of $T_1$ relaxation could be removed. To overcome this limitation magnetization prepared methods have been proposed transferring the double/multi-angle idea into an appropriate preparation of the longitudinal magnetization. This allows a more efficient read out of multiple echoes to reduce the total mapping time. In another technique, the flip angle is calculated from the ratio of a spin echo and a stimulated echo, similar to the double angle methods but with both echoes obtained during the same sequence repetition. In contrast, the actual flip angle technique interleaves two or multiple steady state sequences with significantly differing sequence repetition times (TR). In these $T_1$-weighted gradient echo sequences spoiling of the transverse magnetization after read-out is essential allowing to derive the actual $B_1^+$ from the signal intensity ratio. In case on multi-sequence interleaving also $T_1$ can be estimated additionally to $B_1^+$.

An alternative method uses a set of gradient echo image acquisitions with rather high flip angles. The basic underlying idea is that flip angles of exactly 180° degrees do not generate any transverse magnetization, independent of the $T_1$, $T_2$ relaxation parameters present. Using a couple of measurements, performed at different flip angles around the expected 180° value, allows fitting the expected signal null and via the observed signal intensities. This approach can find an application for mapping small changes in the $B_1^+$ field. However, if the whole dynamic range (e.g., from relatively high to relatively low fields) should be covered, this approach fails.

The second class of mapping approaches transforms the spatially changing $B_1^+$ field into signal phase variations. For these purposes, RF pulse trains (e.g., at least two pulses) are used. In Morrell's approach an initial nonselective nominal 180° RF pulse is applied followed immediately by a nonselective 90° flip about an axis perpendicular to the first. The $B_1$ inhomogeneity causes the actual flip angle to differ from the expected value. It can be shown that the phase of the detectable transverse magnetization is proportional to the actual local $B_1$. However, to compensate for other MR intrinsic phase variations, present in the detection chain, etc., a second scan is performed with the phase of the second RF pulse inverted. This approach works in absence of off-resonance, but demands the incorporation of an off-resonance map in case of significant $B_0$ variations. The magnetization thus generated can be read out using a variety of 3D MR imaging schemes, which could represent a restriction for some applications.

This phase-sensitive method allows imaging over a much wider range of flip angles than double-angle methods. Another phase sensitive approach, recently introduced, is based on the Bloch-Siegert shift, a physical effect known already for a long time. This is an approach of $B_1^+$ related signal phase encoding. After generating transverse magnetization, a second RF pulse of defined duration and shape is applied off-resonant (several kHz) changing the effective precession field for the transverse magnetization, encoding in this way the magnitude of the $B_1^+$ into the MR signal phase. To compensate for other MR intrinsic phase variations, this experiment is repeated without the second RF pulse (or even better with the second RF applied at the off-resonance frequency mirrored to the Larmor frequency). This results in a rather robust approach that is independent of TR, $T_1$. relaxation, flip angle, chemical shift, background field inhomogeneity, and MTC effects. The magnetization thus generated can be read out using a number of MR imaging schemes.

The existing phase-sensitive method for $B_1^+$ mapping, for example Bloch-Siegert shift method, may have a drawback. It is known that any magnetic field change (including $B_0$, gradient field, and each component of RF field) can contribute to image phase. The field estimated by phase-sensitive method should be not $B_1^+$ but $B_1$ which includes $B_x$, $B_y$, and $B_z$ components of $B_1$. These techniques will be accurate for $B_1^+$ mapping only if transmit coils generate perfect circularly polarized RF field cross the object being imaged. In practice, it is impossible at high field strength.

In existing $B_1^+$ mapping MR sequences, measurements are performed for each individual transmit channel or coil in two- or three-dimensions. For an N-coil array where N indicates the number of coils, N transmit field mapping sequences are therefore performed. Unfortunately, these $B_1^+$ mapping MR sequences are relatively slow, and undesirably lengthen the imaging session time.

All of these above mentioned $B_1^+$ mapping methods, including signal intensity-sensitive methods and phase-sensitive methods deal with the magnitude of $B_1^+$. In other words, none of the above mentioned $B_1^+$ mapping methods deal with $B_1^+$ as complex number, that is, both magnitude and phase of $B_1^+$ simultaneously. Compared with conventional $B_1^+$ mapping methods (e.g., using MRI techniques in image domain), the $B_1^+$ mapping techniques in k-space domain described herein provide fast, robust, and accurate $B_1^+$. U.S. Pat. No. 8,502,538 to Dannels et al., entitled "$B_1$ and/or $B_0$ mapping in MRI system using k-space spatial frequency domain filtering with complex pixel by pixel off-resonance phase in the $B_0$ map," describes frequency filtering of spatially modulated or "tagged" MRI data in the spatial frequency k-space domain to estimate $B_1$ and/or $B_0$ maps for an MRI system. However, Dannel's technique requires at least one two-dimensional set of $B_1$ amplitude-tagged MRI data. That is, the technique is based on Tagged MRI technique. Additionally, according to the technique, application of Tagged RF pulse (180) will increase SAR of patients and have a potential risk. Further, the technique uses a sub-set frequency-filter to process the data for estimating transmit field. When there is overlap of frequency spectrum between transmit field and region of interest being imaged, the method may introduce error or artifacts.

In summary, a number of existing techniques have been proposed either encoding $B_1^+$ into the signal intensity or into signal phase. All of these techniques provide methods to estimate the magnitude of transmit field $B_1^+$ via signal intensity and phase. However, all of these techniques show a weakness because these techniques do not estimate phase of transmit field $B_1^+$. In other words, none of the existing techniques provide complex $B_1^+$ mapping. It is clear that the phase of transmit field $B_1^+$ is important for image reconstruction, RF shimming, multi-transmit, and conductivity contrast. Accordingly, in the techniques described below, both the magnitude and phase of $B_1^+$ is encoded into the signal intensity and phase of composite pulses. Furthermore, complex $B_1^+$ (both magnitude and phase) can be estimated in both image domain and k-space domain herein.

MRI System Overview

An example MRI system is described in U.S. Pat. No. 8,502,538 to Dannels et al., entitled "$B_1$ and/or $B_0$ mapping in MRI system using k-space spatial frequency domain filtering with complex pixel by pixel off-resonance phase in the $B_0$ map," issued Aug. 6, 2013, the disclosure of which is hereby incorporated by reference in its entirety. The example MRI system is described below with reference to FIG. 1. This disclosure contemplates that the methods for $B_1^+$ mapping can optionally be implemented using the example MRI system. For example, the MRI system shown in FIG. 1 has a static magnetic field generating unit 12 and a gradient magnetic field generating unit 14 for generating respective magnetic fields in proximity to an object 18. The MRI system also includes a transmitting and receiving unit 16 for irradiating RF pulses to the object and receiving MR signals, a patient table on which the object 18 is placed, and a patient table moving system for moving the table in the body axis direction (e.g., z-axis direction) of the object. The MRI system can also include one or more computing devices such as the example computing device of FIG. 1A. A computing device can be operably coupled to the MRI system, for example, using by any medium that facilitates data exchange between the MRI system and the computing device including, but not limited to, wired, wireless and optical links. For example, a computing device can be configured to convert the MR signals received by the transmitting and receiving unit 16 into k-space data. A computing device can also be configured to generate MR image data from the k-space data by image reconstruction processing. Further, the MRI system can optionally include a workflow setting unit, an imaging operation determining unit, a display unit, an input unit, and a controller system.

The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by the input unit is minimized, an imaging time of each imaging method in the shortest performing order, and the like. The imaging operation determining unit determines whether an imaging operation during a main imaging according to the workflow. This disclosure contemplates that the workflow setting unit and/or the imaging operation unit can be implemented using hardware, software, and or a combination thereof. The display unit displays image data such as local image data, diagnosis image data using display, printer and other displayer. The input unit is manipulated by an operator to input signals to the MRI apparatus to set the imaging method group, the performing order, the imaging condition, and the like. The controller system is composed of a processor and integrally controls the respective units of the MRI system described above.

The static magnetic field generating unit 12 includes a main magnet to generate a strong static magnetic field in proximity to the object. The gradient magnetic field generating unit 14 includes gradient magnetic field coils for generating gradient magnetic fields in an x-axis direction, a y-axis direction, and a z-axis direction, which are orthogonal to each other. The transmitting and receiving unit 16 includes a transmission coil and a transmitter unit for irradiating the RF pulses to the object and a receiving coil and a receiver unit for receiving MR signals generated by the object. Optionally, a transceiver coil having the functions of both the transmission coil and the receiving coil can be used. The receiving coil may be composed of, for example, a so-called array coil in which, for example, a plurality of coil elements are disposed to detect the MR signals generated by the object.

The image reconstruction unit includes an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Example Computing Device

It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 1A:
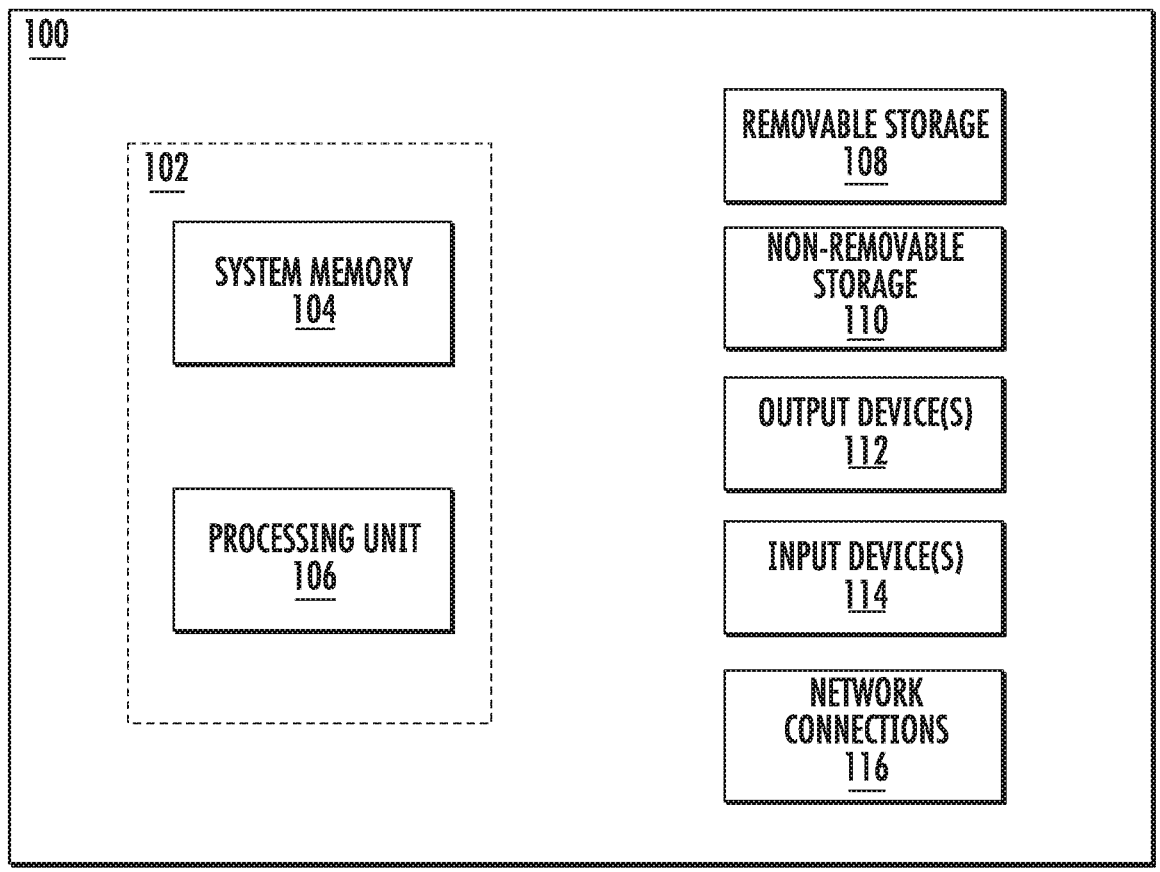
FIG. 1A is a block diagram illustrating an example computing device.

Referring to FIG. 1A, an example computing device 100 upon which embodiments of the invention may be implemented is illustrated. It should be understood that the example computing device 100 is only one example of a suitable computing environment upon which embodiments of the invention may be implemented. Optionally, the computing device 100 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 100 typically includes at least one processing unit 106 and system memory 104. Depending on the exact configuration and type of computing device, system memory 104 may be volatile (such as random access memory (RAM)), non-volatile (such as read-only memory (ROM), flash memory, etc.), or some combination of the two. This most basic configuration is illustrated in FIG. 1A by dashed line 102. The processing unit 106 may be a standard programmable processor that performs arithmetic and logic operations necessary for operation of the computing device 100. The computing device 100 may also include a bus or other communication mechanism for communicating information among various components of the computing device 100.

Computing device 100 may have additional features/functionality. For example, computing device 100 may include additional storage such as removable storage 108 and non-removable storage 110 including, but not limited to, magnetic or optical disks or tapes. Computing device 100 may also contain network connection(s) 116 that allow the device to communicate with other devices. Computing device 100 may also have input device(s) 114 such as a keyboard, mouse, touch screen, etc. Output device(s) 112 such as a display, speakers, printer, etc. may also be included. The additional devices may be connected to the bus in order to facilitate communication of data among the components of the computing device 100. All these devices are well known in the art and need not be discussed at length here.

The processing unit 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the processing unit 106 for execution. Example tangible, computer-readable media may include, but is not limited to, volatile media, non-volatile media, removable media and non-removable media implemented in any method or technology for storage of information such as computer readable instructions, data structures, program modules or other data. System memory 104, removable storage 108, and non-removable storage 110 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 106 may execute program code stored in the system memory 104. For example, the bus may carry data to the system memory 104, from which the processing unit 106 receives and executes instructions. The data received by the system memory 104 may optionally be stored on the removable storage 108 or the non-removable storage 110 before or after execution by the processing unit 106.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Theory

Although nuclear spins interact with each other in the NMR experiment, many experiments assume that: (1) The influence of atomic electrons on local static field strength (such as chemical shift) is negligible; (2) The interaction between neighboring nuclei as well as between nuclei and the lattice is neglected, i.e., the longitudinal relaxation and the transverse relaxation times are much longer compared to the considered time intervals (several milliseconds). According to Bloch equation, nuclear magnetization $\vec{M}$ in laboratory frame obeys the equation below:

$$\frac{d\vec{M}}{dt} = \gamma(\vec{M} \times \vec{B}_{eff}) \quad (2)$$

where $\gamma$ is the magnetogyric ratio.

$$\vec{B}_{eff} = B_0 \vec{k} + \vec{B}_1 + \vec{G} \cdot \vec{r} \quad (3)$$

where $B_0$ is static magnetic field strength; $\vec{B}_1$ is radiofrequency magnetic field strength of the transmission coil, $\vec{G}$ is the system gradient strength; $\vec{r}$ is spatial location vector. The $\vec{i}$, $\vec{j}$ and $\vec{k}$ are the unit vectors in the Cartesian coordinate system. In three components of $\vec{B}_1$, any transverse components of $B_x$ and $B_y$ of transmit coils can contribute to MR signal. That is, a positive circularly polarized component of the transmit field $B_1^+\frac{1}{2}(B_x+i\bullet B_y)$ can excite near spin and then contribute to MR signal.

The components $M_x$ and $M_y$ of nuclear magnetization $\vec{M}$ can be stimated by an analytical, empirical, and/or approximated solution of Bloch Equations, e.g., Eq. (2). For example, analytical solutions to Bloch Equations for fast spin echo are described in Lukzen N N, Saveloy A A, Analytical derivation of multiple spin echo amplitudes with arbitrary refocusing angle, J Magn Reson 2007, 185(1):71-6. Numerical solutions to Bloch Equations are described in Murase K., Tanki N., Numerical solutions to the time-dependent Bloch equations revisited, Magn Reson Imaging 2011; 29(1):126-31. High tip angle approximation solutions to Bloch Equations are described in Boulant N1, Hoult D I, High tip angle approximation based on a modified Bloch-Riccati equation, Magn Reson Med 2012; 67(2):339-43. In other words, the simulation can be performed using Bloch Equations. Additionally, a solution of the Bloch's Equations can be at least one of an analytic solution, a numerical solution, or an approximation solution.

The complex signal is given by:

$$\text{Signal} \propto M_x + i \cdot M_y \quad (4)$$

The magnitude of signal is given by:

$$|\text{Signal}| \propto \sqrt{M_x^2 + M_y^2} \quad (5)$$

The phase φ of signal is given by:

$$\varphi = \arctan\left(\frac{M_y}{M_x}\right) \quad (6)$$

A double flip angle method for estimating $B_1^+$ mapping of transmit coil

For a gradient echo (GRE) sequence with excitation flip angle α(x), the transmission field for non-interacting spins without transverse coherence, and assuming that the repetition time TR>>longitudinal relaxation time $T_1$, can be written as follows:

$$B_1^+ = \frac{1}{\gamma\tau} \cdot \arccos\left(\frac{\lambda}{2}\right) \quad (7)$$

where γ is the magneto-gyric ratio, $$\lambda = \frac{SI_2(x)}{SI_1(x)} = \frac{\sin\alpha_2(x)}{\sin\alpha_1(x)}$$

is the ratio of signal intensities of two GRE images which are acquired with different excitation flip angles such that $\alpha_2(x)=2\alpha_1(x)$ while maintaining the other imaging parameters (TE, TR). τ is the duration of the RF pulse, and $B_1^+$ is a positive circularly polarized component of the RF field of transmit coil, which rotates in the same direction as nuclear spins precess. Generally, the two gradient echo images are choosen with the nominal exciting flip angle of 60° and 120°, respectively, because at these angles the measured $B_1^+$ map will have high SNR which is close to the SNR of the image with the exciting flip angle of 60°. $B_1^+$ map can be estimated by Eq (7).

Various factors, such as transmit coil configuration, uncompensated eddy currents, wave behavior and object positioning, generate inhomogeneous transmit field. The nominal flip angle of α is defined by averaged flip angles cross volume being imaged. Thus, the actual flip angle should be a function of location. The goal of $B_1^+$ mapping is to estimate the function of flip angle as a space distribution. In most MRI applications, only magnitude images are used. However, phase information is very fundamental, if not more fundamental than magnitude, considering the fact that MR signal magnitude changes are often ultimately due to spin "de-phasing". In k-space, phase of the raw data has been demonstrated to carry more information than magnitude for visualization. Thus, MR image phase is very important. The MR image phase is given:

$$\phi_{image} = \Sigma_i^N \phi_{Ti} + \phi_{B0} + \phi_{Rec} + \phi_{syn} \quad (8)$$

Where $\phi_{Ti}$ is the phase of the $B_1^+$ field for the $i^{th}$ RF pulse. The RF pulse can be either on-resonance or off-resonance RF pulse. This phase $\phi_{syn}$ is a constant, and therefore assumed to be zero. $\phi_{B0}$ is the phase accumulation of phases which result from at least one of $B_0$ inhomogeneity, flow, eddy current., and chemical shift. The receive phase, $\phi_{Rec}$, is a phase of the receive coil which is spatial function at the high field strength. $\phi_{syn}$ is a reference phase which is the sum of reference phases from transmitter radiofrequency synthesizer, receiver radiofrequency synthesizer, and digitizer. Thus, estimating the phase of $B_1^+$ is very important and useful in MRI.

Methods and Results

Figure 2:
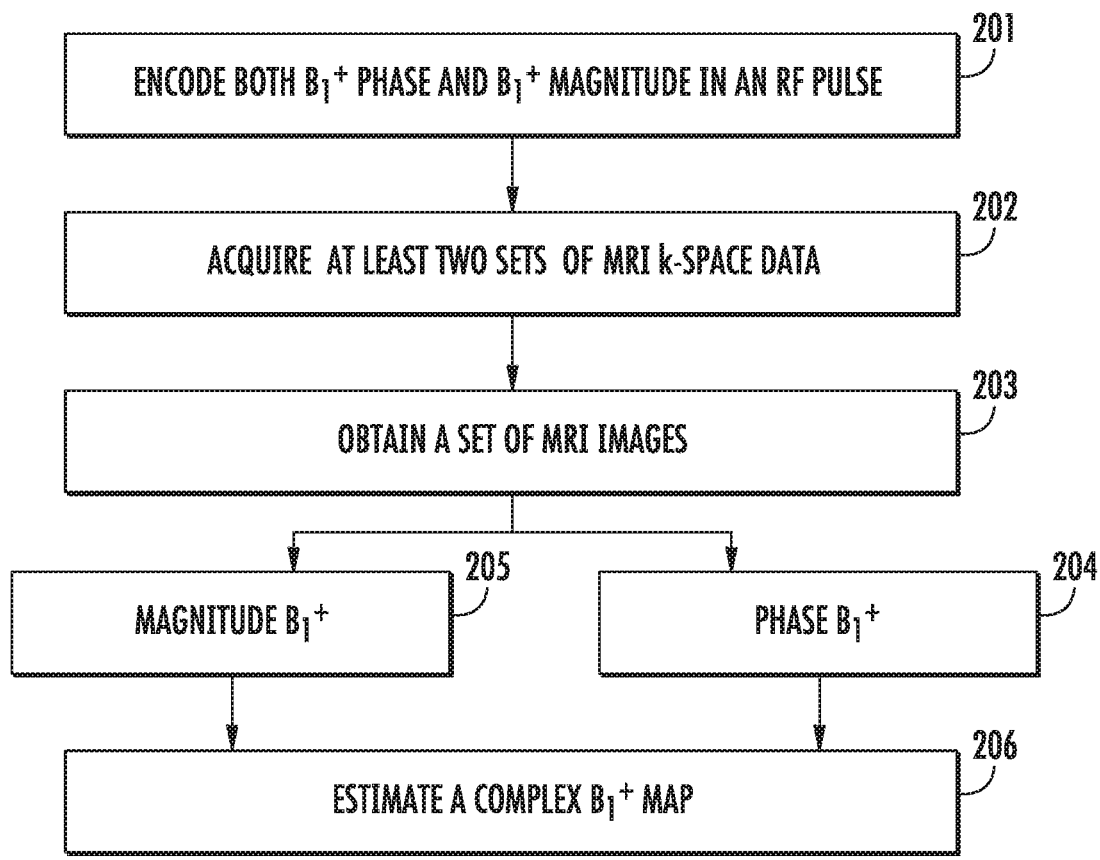
FIG. 2 is a flow chart illustrating example operations for complex $B_1^+$ mapping in the image domain according to an implementation described herein.

Referring now to FIG. 2, a flow chart illustrating example operations for complex $B_1^+$ mapping in the image domain according to an example implementation is shown. In order to obtain complex $B_1^+$ mapping of a transmit coil of an MRI system with a given RF pulse type, both $B_1^+$ phase and $B_1^+$ magnitude of the transmit coil being estimated are encoded into at least one RF pulse at step 201. The RF pulse can be an excitation RF pulse or a reference RF pulse as described above. Optionally, in some implementations, the RF pulse can be a single RF pulse. In other words, a single RF pulse can have both encoded $B_1$ phase and encoded $B_1$ magnitude. Alternatively or additionally, in other implementations, the RF pulse can optionally be a plurality of RF pulses. Optionally, the RF pulses can include at least one RF pulse having encoded $B_1$ phase and at least one RF pulse having encoded $B_1$ magnitude. The RF pulse having encoded $B_1$ phase and the RF pulse having encoded $B_1$ magnitude can be the same or different RF pulses. This disclosure contemplates that a plurality of phase and magnitude encoded RF pulses can combine with themselves (and optionally other RF pulses) to create a pulse sequence for image acquisition.

Alternatively or additionally, the $B_1$ phase and/or $B_1$ magnitude encoding can be accomplished using one or more pulse sequences. For example, in some implementations, a single pulse sequence can be used, and at least two sets complex of k-space data (e.g., at least two k-space images) can be acquired, where each set of complex k-space data has at least one RF pulse with different encoded $B_1$ phase and/or different encoded $B_1$ magnitude as compared to the other set of complex k-space data. In this implementation, each set of complex k-space data includes at least an RF pulse having encoded $B_1$ phase and at least an RF pulse having encoded $B_1$ magnitude. As described above, the RF pulses having encoded $B_1$ phase and the RF pulse having encoded $B_1$ magnitude can be the same RF pulse or different RF pulses. In addition, the complex $B_1^+$ map can be estimated based on the at least two sets complex of k-space data (e.g., at least two k-space images) with different encoded $B_1$ phases and different encoded $B_1$ magnitudes. This disclosure contemplates that more than two sets of complex k-space data (e.g., 3, 4, 5, 6, etc. sets of complex k-space data) can be acquired.

In other implementations, a plurality of pulse sequences can be used, where at least one pulse sequence has at least two RF pulses having different encoded $B_1$ phases and at least one pulse sequence has at least two RF pulses having different encoded $B_1$ magnitudes. This disclosure contemplates that more than two pulse sequences (e.g., 3, 4, 5, 6, etc. pulse sequences) can be used. At least wo sets complex of k-space data (e.g., at least two k-space images) including RF pulses having different encoded $B_1$ phases can be acquired based on one of the pulse sequences. A $B_1^+$ phase map can be determined from these sets of complex k-space data. In addition, at least two sets complex of k-space data (e.g., at least k-space images) including at least two RF pulses having different encoded $B_1$ magnitudes can be acquired based on the other pulse sequence. A $B_1^+$ magnitude map can be determined from these sets of complex k-space data. In addition, the complex $B_1^+$ map can be estimated based on the $B_1^+$ phase map and the $B_1^+$ magnitude map. Similar to above, this disclosure contemplates that more than two sets of complex k-space data (e.g., 3, 4, 5, 6, etc. sets of complex k-space data) can be acquired.

The RF pulse type can be one of rectangle RF pulse, truncated-sine RF pulse, sinc RF pulse, Gaussian RF pulse, adiabatic RF pulse, Hermite RF pulse, or Shinnar-Le Roux RF pulses. It should be understood that the RF pulse types above a provided only as examples and should not be limiting. This disclosure contemplates that the RF pulse can be another pulse type. Since complex $B_1^+$ mapping of the transmit coil strongly depends on the RF pulse type and configuration, the encoded RF pulse can be identical to, or very close to, the RF pulses being estimated, except the phase and magnitude of the encoded RF pulses. For example, the first image at the flip angle of α and the second image at the flip angle of 2α can be used to encode $B_1^+$ magnitude in the RF pulse for estimate $B_1^+$ magnitude in a double flip angle method [Insko E K et al, 1993; U.S. Pat. No. 7,446,526]. As used herein, "encoded $B_1^+$ phase and encoded $B_1^+$ magnitude" means that the pulse sequence which is used to estimate complex $B_1^+$ mapping includes variation of both $B_1^+$ phase and $B_1^+$ magnitude in the encoded RF pulse or encoded RF reference pulses. The pulse sequence is configured to excite precessing nuclear spins in magnetic resonance (MR) nuclei, and a plurality of MR signals representing nuclear MR signals arising from the precessing nuclear spins in the MR nuclei can be detected using the MRI system.

At step 202, at least two sets of k-space data (e.g., at least two k-space images) including the encoded RF pulse(s) are acquired with the MRI system. For example, at least two sets of complex k-space data including an RF pulse having encoded $B_1$ phase and at least two sets of complex k-space data including an RF pulse having encoded $B_1$ magnitude can be acquired. Each set of complex k-space data including an RF pulse having encoded $B_1$ phase can have a different encoded $B_1$ phase. For example, each set of complex k-space data can be a complex k-space image with different encoded $B_1$ phase, i.e., at least two complex k-space images, each complex k-space image including an RF pulse having a different encoded $B_1$ phase as compared to the other complex k-space image. Additionally, each set of complex k-space data including an RF pulse having encoded $B_1$ magnitude can have a different encoded $B_1$ magnitude. For example, each set of complex k-space data can be a complex k-space image with different encoded $B_1$ magnitude, i.e., at least complex k-space images, each complex k-space image including an RF pulse having a different encoded $B_1$ magnitude as compared to the other complex k-space image. One or more of (e.g., each of) the sets of complex k-space data can include full k-space or a portion of k-space. As used herein, the complex k-space data can optionally be a complex k-space image.

At step 203, a series of images with different encoded $B_1^+$ phases and/or $B_1^+$ magnitudes are obtained. For example, each of the at least two sets of complex k-space data including at least two RF pulses having different encoded $B_1$ phases can be transformed into a respective image (e.g., 204 in FIG. 2) in an image domain (i.e., two images, each image having a different encoded $B_1$ phase as compared to the other image). A $B_1^+$ phase map can be estimated from the respective images. In addition, each of the at least two sets of complex k-space data including at least two RF pulses having different encoded $B_1$ magnitudes can be transformed into a respective image (e.g., 205 in FIG. 2) in the image domain (i.e., two images, each image having a different encoded $B_1$ magnitude as compared to the other image). A $B_1^+$ magnitude map can be estimated from the respective images. This disclosure contemplates that the complex k-space data can be transformed into the image domain using an inverse Fourier transform such as an inverse 2D or 3D FFT, for example. At 206, the complex $B_1^+$ map of at least a portion of the transmit coil of the MRI system can be estimated based on the images. For example, the complex $B_1^+$ map can be determined from the $B_1^+$ phase map and the $B_1^+$ magnitude map as described above. The complex $B_1^+$ map can optionally be stored in a memory for later use. In some implementations, the complex $B_1^+$ map is estimated using the relationship between a complex MR signal and complex $B_1^+$ mapping which is created by Bloch Equations. That is, the magnitude and phase of transmit field $B_1^+$ can be estimated using Bloch Equation from these images, respectively. Furthermore, the complex $B_1^+$ map can be estimated using an analytic, empirical, and/or approximated solution of Bloch Equations with encoded $B_1^+$ phase and $B_1^+$ magnitude. Alternatively or additionally, in some implementations, $B_1^+$ magnitude can be estimated using at least one of a double flip angle method, dual pulse spin echo, actual flip angle imaging, stead state method, dual refocusing echo acquisition mode (DREAM), Bloch Siegert shift method and phase sensitive method.

As described above, the phase change in Bloch-Siegert shift method includes the contribution of each component of $B_1$, including $B_x$, $B_y$, and $B_z$. If the phase is assumed to be the contribution of $B_1^+$, it is only an approximation. For surface coil or non-quadrature coil, the approximation may introduce a large error. However, it is a good approximation for quadrature birdcage coil. According to this disclosure, an off-resonant (e.g., by several kHz) RF pulse can be applied to change the effective precession field for the transverse magnetization, and encode phase of the $B_1^+$ into the MR signal phase. In some implementations, the RF pulse can be on-resonance excitation. Alternatively or additionally, in other implementations, the RF pulse can be off-resonance excitation.

Figure 3A:
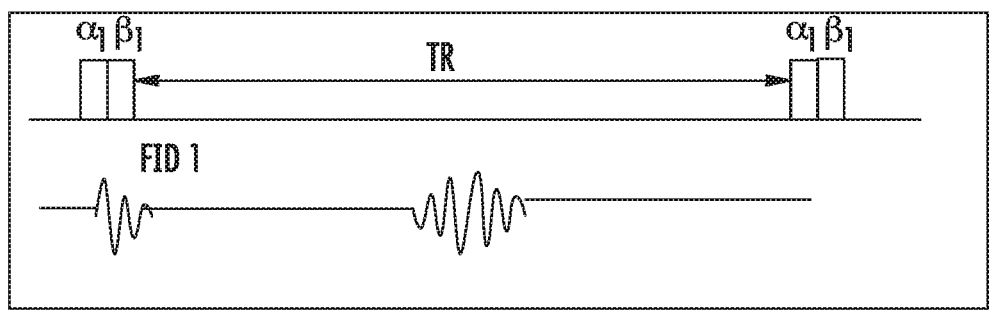
FIGS. 3A and 3B illustrate encoding $B_1^+$ phase and $B_1^+$ magnitude in RF pulses according to an implementation described herein.
Figure 3B:
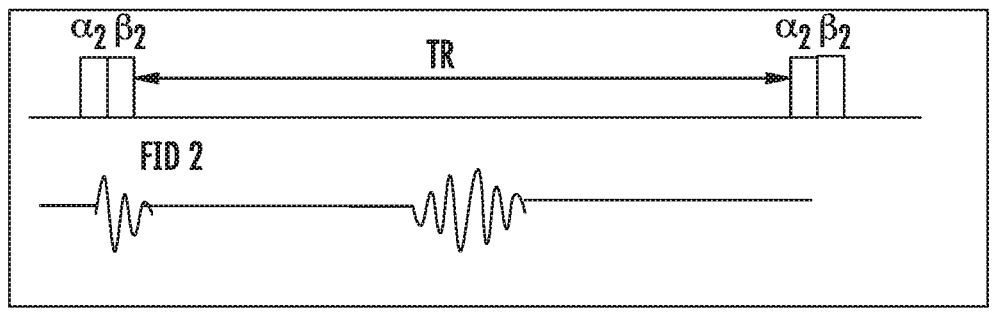

Encoding both $B_1^+$ phase and $B_1^+$ magnitude of the transmit coil being estimated into MR RF pulse sequences and building the relationship between complex MR signal and complex $B_1^+$ are prerequisites for estimating complex $B_1^+$ mapping of transmit coils. Theoretically, the complex $B_1^+$ mapping can be estimated by using an analytic and/or empirical and/or approximated solution of Bloch Equations with different encoded $B_1$ phases and $B_1$ magnitudes. In practice, the complex $B_1^+$ mapping may be limited by encoded $B_1$ phase and encoded $B_1$ magnitude methods, as well as solution to the Bloch Equation in short time. FIGS. 3A and 3B illustrate examples for encoding different $B_1$ phases and different $B_1$ magnitudes in RF pulses. As used herein, the RF pulse $\alpha_1$ can be used as "a carrier" of MR signal. The RF pulse $\alpha_1$ can include at least one RF pulse or one composite RF pulse. The RF pulse $\alpha_1$ can be an arbitray RF pulse. In some implementations, it can be the same as the RF pulse being estimated for complex $B_1^+$ mapping to simplify the procedure for estimating $B_1^+$ mapping. The RF pulses $\beta_1$ and $\beta_2$ can include one or more of the following characteristics. The RF pulses $\beta_1$ and $\beta_2$ can include at least one RF pulse or one composite RF pulse. The composite RF pulse can be a series of different RF pulses. The RF pulses $\beta_1$ and $\beta_2$ can include at lease one of the RF pulse which complex $B_1^+$ mapping will be estimated by MR images. Both $B_1$ phase and $B_1$ magnitude of the transmit coils being estimated can be simultaneously or separately encoded in at least one of the estimated RF pulse(s) in the RF pulses $\beta_1$ and $\beta_2$. The RF pulses $\beta_1$ and $\beta_2$ can be either on-resonance or off-resonance RF pulses. The encoded $B_1$ phase and $B_1$ magnitude of the transmit coils in RF pulses $\beta_1$ can be different from those in RF pulses $\beta_2$ for complex $B_1^+$ mapping being estimated. The complex $B_1^+$ mapping can be estimated using an analytic and/or empirical and/or approximated solution of Bloch Equations of the pulse sequences (e.g., the pulse sequences of FIG. 3A or 3B). In FIGS. 3A and 3B, the procedure for estimating complex $B_1^+$ mapping is shown for two images acquired with two sequences. In practice, the complex $B_1^+$ mapping can be also estimated by at least two images which can be acquired with one or more sequences.

For example, to simplify the estimation of complex $B_1^+$ mapping, both the magnitude and the phase of RF pulse $\alpha_1$ can be same as those of RF pulse $\beta_1$. Additionally, both the pulses excite at the on-resonance frequency in FIG. 3A. In this case, $B_1^+$ magnitude of the transmit coils has been encoded into this sequence. In FIG. 3B, the magnitude of RF pulse $\alpha_2$ is same as that of the RF pulses of both $\beta_2$ and $\alpha_1$. But the RF pulse $\alpha_2$ excites at the on-resonance frequency and the RF pulse $\beta_2$ excites at the oft-resonance frequency which far away from on-resonance frequency by several kHz. The $B_1^+$ magnitude of the transmit coils can estimated from magnitudes of MR signal acquired by these two sequences. The phase $B_1^+$ of the transmit coils can be estimated from phases of MR signal acquired by these two sequences. Finally, the complex $B_1^+$ mapping can be also estimated. Thus, different $B_1$ phases and different $B_1$ magnitudes are encoded into the two sequences of FIGS. 3A and 3B through the RF pulses $\beta_1$ and $\beta_2$ simultaneously. As a result, the number of images for estimating complex $B_1^+$ mapping is reduced to be minimal.

Figure 4:
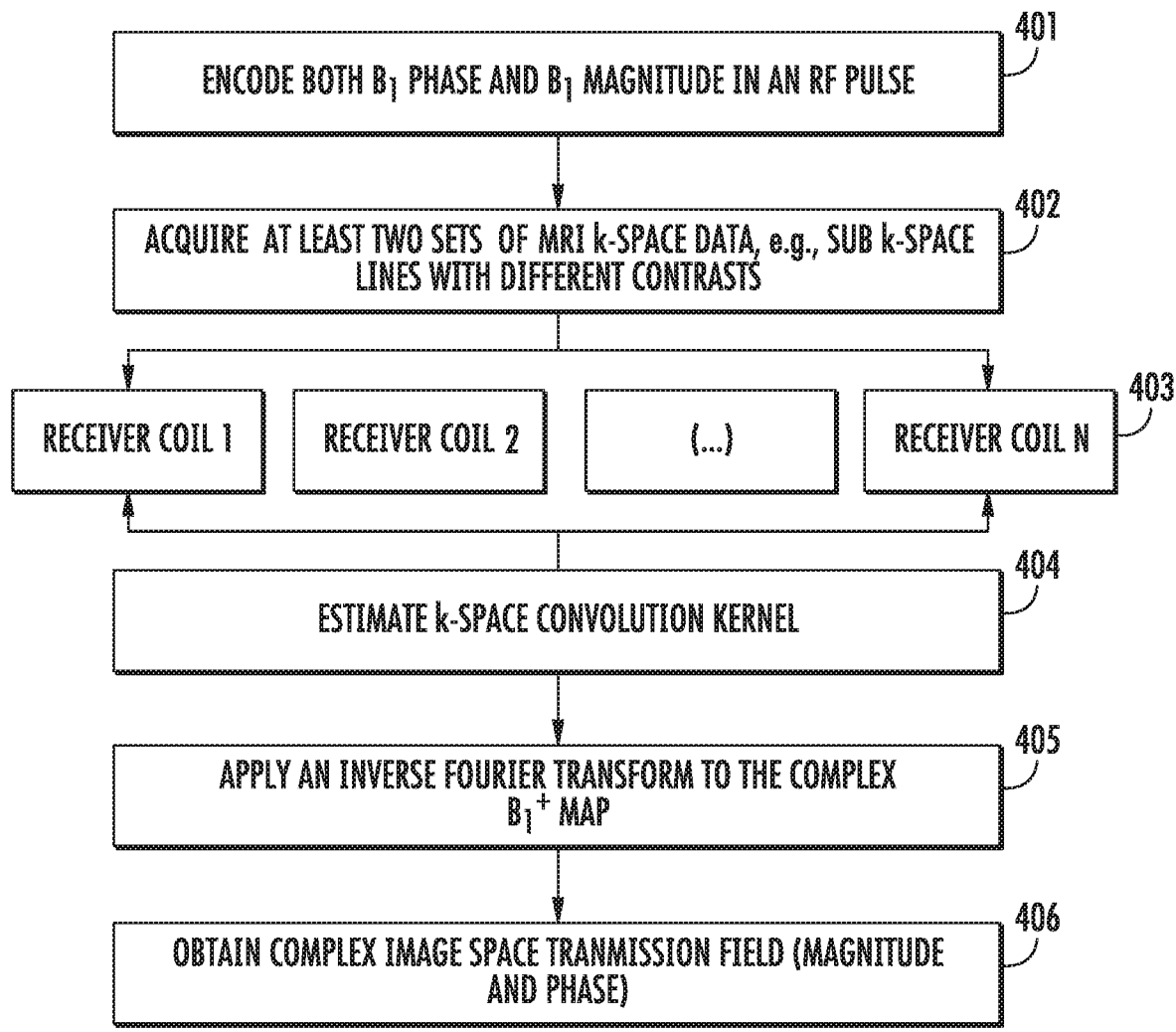
FIG. 4 is a flow chart illustrating example operations for complex $B_1^+$ mapping in the K-space domain according to an implementation described herein.

Referring now to FIG. 4, a flow chart illustrating example operations for complex $B_1^+$ mapping in the K-space domain according to an example implementation described herein is shown. In order to obtain complex $B_1^+$ mapping of a transmit coil of an MRI system with a given RF pulse type, both $B_1^+$ phase and $B_1^+$ magnitude of the transmit coil being estimated are encoded into at least one RF pulse at step 401. Optionally, in some implementations, the RF pulse can be a single RF pulse. In other words, a single RF pulse can have both encoded $B_1$ phase and encoded $B_1$ magnitude. Alternatively or additionally, in other implementations, the RF pulse can optionally be a plurality of RF pulses. Optionally, the RF pulses can include at least one RF pulse having encoded $B_1$ phase and at least one RF pulse having encoded $B_1$ magnitude. The RF pulse having encoded $B_1$ phase and the RF pulse having encoded $B_1$ magnitude can be the same or different RF pulses. This disclosure contemplates that a plurality of phase and magnitude encoded RF pulses can combine with themselves (and optionally other RF pulses) to create a pulse sequence for image acquisition. Optionally, as described above, a plurality of pulse sequences can be used. As described above, the pulse sequence is configured to excite precessing nuclear spins in magnetic resonance (MR) nuclei, and a plurality of MR signals representing nuclear MR signals arising from the precessing nuclear spins in the MR nuclei can be detected using the MRI system.

At step 402, a set of k-space data including the encoded RF pulse is acquired with the MRI system. For example, at least two sets of complex k-space data including an RF pulse having encoded $B_1$ phase and at least two sets of complex k-space data including an RF pulse having encoded $B_1$ magnitude can be acquired. As discussed above, each set of complex k-space data including an RF pulse having encoded $B_1$ phase can have a different encoded $B_1$ phase. Additionally, each set of complex k-space data including an RF pulse having encoded $B_1$ magnitude can have a different encoded $B_1$ magnitude. The sets of complex k-space data can include full k-space or a portion of k-space. As used herein, the complex k-space data can optionally be a complex k-space image. K-space data from multiple receive coils can be lumped together to estimate the complex $B_1^+$ mapping as shown by 403 in FIG. 4. At step 404, a k-space domain convolution kernel between k-space of the acquired sets of complex k-space data can be estimated. For example, the k-space domain convolution kernel can be estimated using a fitting algorithm. The complex $B_1^+$ map can be estimated from the k-space domain convolution kernel. As described herein, a k-space approach to estimate the complex $B_1^+$ map in double flip-angle method according to one implementation is provided, which eliminates the pixel-wise division completely, A k-space convolution kernel c(k) between two k-space of image A and B: $F(A)=F(B) \otimes c(k)$ can be estimated. Convolution kernel c(k) can be calculated using k-space data fitting method, for example, the same way as the kernel estimation in GRAPPA/SPIRiT algorithm. Since transmission field is independent of the receive sensitivity, it is possible to use a single channel in a phased-array coil to estimate the transmission field. Every k-space point of a single channel contributes an independent linear equation. If all channels of a phase-array receive coil are lumped together as shown by 403 in FIG. 4, a better estimation can be achieved because there are more equations. According to convolution theorem, the convolution kernel is the Fourier transform of the pixel-wise division between two images, i.e.: the complex $B_1^+$ map is proportional to $\arccos(F^{-1}(c(k)*)/2)$.

At step 405, the complex $B_1^+$ map can be transformed into an image domain. This disclosure contemplates that the complex k-space data can be transformed into the image domain using an inverse Fourier transform such as an inverse 2D or 3D FFT, for example. Then, at step 406, the complex $B_1^+$ map in the image domain is obtained.

Alternatively or additionally, the MRI system described herein can include a plurality of RF transmit channels or elements. The method can optionally include, using the complex $B_1^+$ map of each of the RF transmit channels or elements, performing RF shimming or tailored RF shimming.

Alternatively or additionally, the methods described herein (e.g., the methods described with regard to FIG. 2 and/or FIG. 4) can optionally include, using the complex $B_1^+$ map, improving the precision of quantitative MRI. For example, the quantitative MRI can include, but is not limited to, $T_1$ mapping, $T_2$ imaging, water/fat fraction, molecule concentration for magnetic resonance spectroscopy (MRS), and/or magnetic resonance spectroscopy imaging (MRSI).

Alternatively or additionally, the methods described herein (e.g., the methods described with regard to FIG. 2 and/or FIG. 4) can optionally include, using the complex $B_1^+$ map, generating a new MRI contrast at different frequencies. For example, the new MRI contrast can include, but is not limited to, conductivity or permittivity contrast.

Alternatively or additionally, the methods described herein (e.g., the methods described with regard to FIG. 2 and/or FIG. 4) can optionally include, using the complex $B_1^+$ map, designing or evaluating the at least the portion of the transmit coil of the MRI system.

Alternatively or additionally, the methods described herein (e.g., the methods described with regard to FIG. 2 and/or FIG. 4) can optionally include, using the complex $B_1^+$ map, performing quality control of the at least portion of the transmit coil of the MRI system.

Alternatively or additionally, the at least two complex images described herein can have different contrasts.

Alternatively or additionally, the at least two complex images described herein can be acquired using different MRI system configurations. For example, the different MRI system configurations include, but are not limited to, different coil elements of a receive coil, different receive coils, and/or different gradient encoding strategies.

Alternatively or additionally, the at least two complex images described herein can be acquired using different imaging parameters. For example, the imaging parameters can include, but are not limited to, repetition time (TR), echo time (TE), flip angle, inversion recovery time, and/or receiver bandwidth.

Alternatively or additionally, the complex $B_1^+$ map can be estimated for a global or regional region of interest (ROI).

Alternatively or additionally, the methods described herein (e.g., the methods described with regard to FIG. 2 and/or FIG. 4) can optionally include displaying the complex $B_1^+$ map for visual observation by a user of the MRI system.

Alternatively or additionally, the methods described herein (e.g., the methods described with regard to FIG. 2 and/or FIG. 4) can optionally include, using the complex $B_1^+$ map, performing image compensation to a diagnostic image acquired by the MRI system.

Alternatively or additionally, the methods described herein (e.g., the methods described with regard to FIG. 2 and/or FIG. 4) can optionally include, using the complex $B_1^+$ map, determining a parameter controlling RF transmission of the MRI system.

Alternatively or additionally, the methods described herein (e.g., the methods described with regard to FIG. 2 and/or FIG. 4) can optionally include, using the complex $B_1^+$ map, improving the precision of quantitative MRI. For example, the quantitative MRI can include, but is not limited to, $T_1$ mapping, $T_2$ imaging, water/fat fraction, molecule concentration for magnetic resonance spectroscopy (MRS), and/or magnetic resonance spectroscopy imaging (MRSI).

Alternatively or additionally, the methods described herein (e.g., the methods described with regard to FIG. 2 and/or FIG. 4) can optionally include, using the complex $B_1^+$ map, generating a new MRI contrast at different frequencies. For example, the new MRI contrast can include, but is not limited to, conductivity or permittivity contrast.

Alternatively or additionally, the methods described herein (e.g., the methods described with regard to FIG. 2 and/or FIG. 4) can optionally include, using the complex $B_1^+$ map, designing or evaluating the at least the portion of the transmit coil of the MRI system.

Alternatively or additionally, the methods described herein (e.g., the methods described with regard to FIG. 2 and/or FIG. 4) can optionally include, using the complex $B_1^+$ map, performing quality control of the at least the portion of the transmit coil of the MRI system.

Alternatively or additionally, parallel transmit techniques can optionally be derived from an amplitude and a phase of the complex $B_1^+$ of the MRI system.

Alternatively or additionally, the methods described herein (e.g., the methods described with regard to FIG. 2 and/or FIG. 4) can optionally include, using the complex $B_1^+$, correcting MR signal inhomogeneity caused by transmit coils of the MRI system. Conventional $B_1^+$ mapping methods are just used for mapping the magnitude of excitation RF pulse in image domain. The systems and methods described herein: (1) can estimate $B_1^+$ mapping from both image domain and k-space domain; (2) can extend $B_1^+$ mapping from excitation RF pulse to any RF pulse, including excitation RF pulse, refocusing RF pulse and magnetization preparation RF pulse; (3) can estimate $B_1^+$ mapping from real (magnitude) to complex (including magnitude and phase).

Alternatively or additionally, the complex $B_1^+$ can be applied to improve performance of simultaneous multi-slice imaging. Simultaneous multi-slice (SMS) imaging using parallel image reconstruction is a promising imaging technique because an acceleration factor equal to the number of simultaneously excited slices can be reached. Therefore, SMS imaging significantly decreases the amount of time for acquiring image data. Comparing to traditional parallel imaging techniques, SMS imaging has the following advantages: (1) it is applicable to imaging pulse sequences that sample multiple lines of k-space following each RF excitation; and (2) it allows more reliable separation of aliased pixels.

Even though multiple slices are excited using SMS imaging, only one image is acquired, and all slices overlap on each other. Specific data acquisition and corresponding reconstruction strategies are employed to resolve each individual image. Three techniques are used for SMS spatial encoding: RF phase encoding, gradient phase encoding, and coil encoding. For multiband excitations, i.e., multiple slice excitation, shifts between simultaneously excited slices can be accomplished by applying individual phase cycling patterns to each frequency band. The number of different multiband RF pulses that are required depend on the number of simultaneous slices. Simultaneously excited slices can also be resolved by the gradient phase encoding along the slice direction. The third technique (i.e., receiver coil encoding) is also known as parallel MRI and is an integral part of modern clinical MRI. Receiver sensitivity phase encoding can be used to achieve a substantial acceleration, compared with receiver sensitivity magnitude encoding only. In practice, modern SMS acquisitions use a combination of coil encoding with either RF encoding or gradient encoding to resolve the slice direction. The complex $B_1^+$ map described herein can be used to achieve a substantial acceleration in SMS acquisitions. As a result, the performance of SMS acquisitions, including acceleration factors and image quality, can be greatly improved using the complex $B_1^+$ map.

Figure 5:
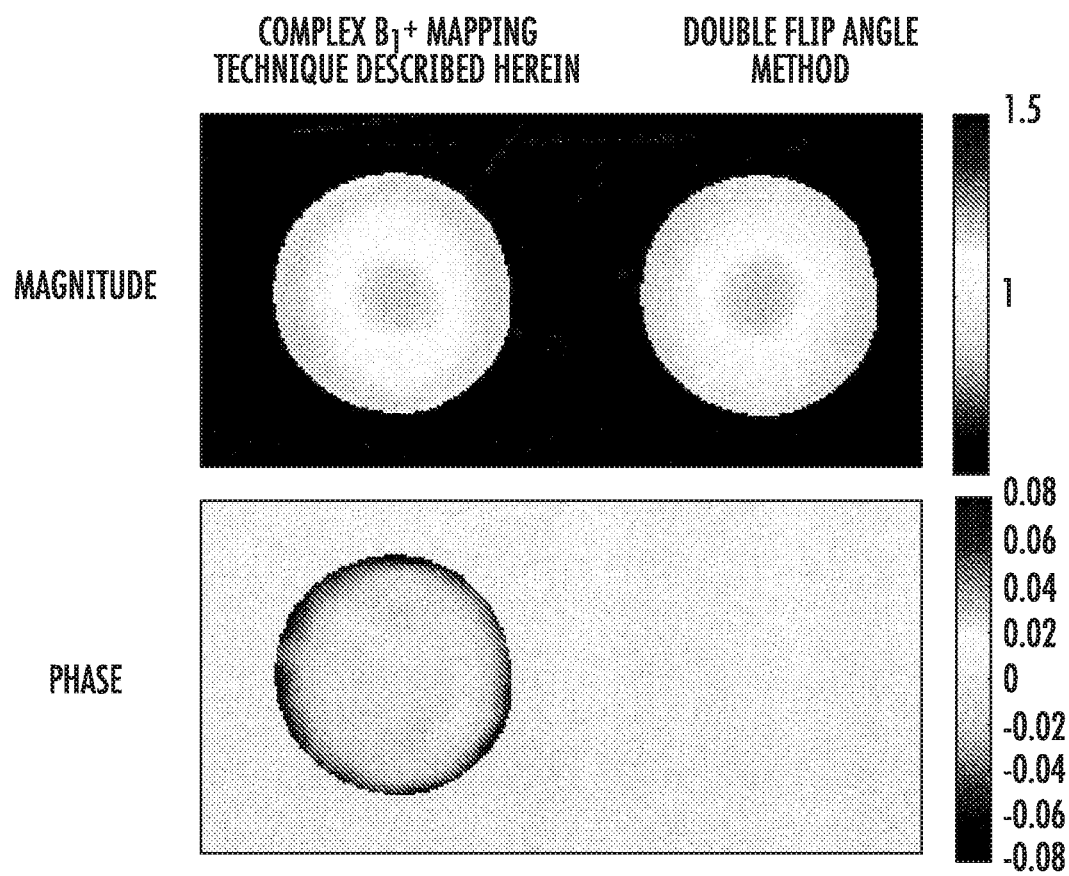
FIG. 5 illustrates a comparison of the $B_1^+$ mapping results in a phantom object using a $B_1^+$ mapping technique described herein (left-hand side of FIG. 5) and using a conventional double flip angle method (right-hand side of FIG. 5).
Figure 6:
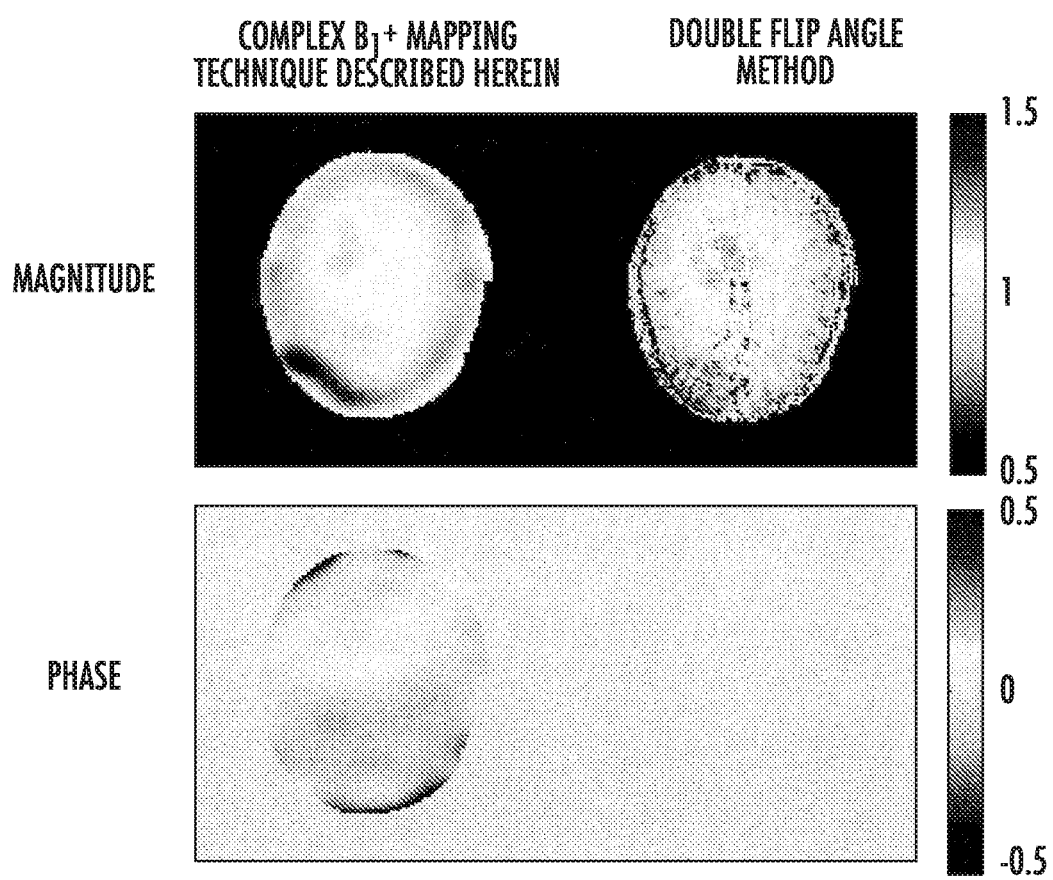
FIG. 6 illustrates a comparison of the $B_1^+$ mapping results in an in vivo human brain using a $B_1^+$ mapping technique described herein (left-hand side of FIG. 6) and using a conventional double flip angle method (right-hand side of FIG. 6).

FIGS. 5 and 6 illustrate comparisons of the $B_1^+$ mapping results in a phantom and in vivo human brain, respectively, using a $B_1^+$ mapping technique described herein (left-hand side of FIGS. 5 and 6) and using a conventional double flip angle method (right-hand side of FIGS. 5 and 6). As shown in FIGS. 5 and 6, the conventional double flip angle method does not have the estimated phase of the $BB_1^+$ mapping. There are many factors influencing the accuracy or practical usefulness of $B_1^+$ mapping techniques, including coil configuration, a subject or object, and/or RF pulse configuration (shape, duration, etc.). Accurate $B_1^+$ mapping should be estimated in real time for subject and RF pulse configuration, e.g., most of conventional $B_1^+$ mapping methods, such as double flip angle method require image space pixel-wise division. When SNR is low, the common coil combine algorithm introduces signal bias as well as complex noise behavior due to small pixel value appear as denominators. Therefore, the pixel-wise division based $B_1^+$ map may be problematic. As described herein, a method utilizing k-space data to estimate $B_1^+$ map is described instead. According to convolution theorem, the image space pixel-wise multiply/division can be calculated in k-space as convolution. The method described herein utilizes k-space convolution to substitute image space pixel-wise division. Therefore, it does not have instabilities caused by small denominators. In addition, it avoids coil combine completely because it uses k-space data directly. Therefore, the method described herein easily combines with various sequences, k-space trajectories, and parallel imaging techniques to improve temporal-spatial resolution, accuracy and precision of $B_1^+$ maps.

Since the convolution kernel has finite support in k-space, i.e., the kernel size may be smaller than the k-space size, there is an intrinsic low-pass filtering effect in the method described herein. Comparing to the conventional methods, the method described herein finds the optimal solution at a given filter bandwidth in the least-square sense. Therefore, the method described herein is more robust when the SNR is low. It also avoids the bias introduced by coil combine which is a nonlinear process when the SNR is low.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for determining spatial distribution of magnitude and absolute phase of radio frequency (RF) transmit field $B_1^+$ in a magnetic resonance imaging (MRI) system, comprising:
    applying at least one pulse sequence configured to excite precessing nuclear spins in magnetic resonance (MR) nuclei, the at least one pulse sequence comprising at least one RF pulse having encoded $B_1$ absolute phase and encoded $B_1$ magnitude, wherein the at least one RF pulse excites at on-resonance frequency;
    detecting a plurality of MR signals representing nuclear MR signals arising from the precessing nuclear spins in the MR nuclei;
    acquiring at least two sets of complex k-space data from the MR signals, the at least two sets of complex k-space data including an RF pulse having encoded $B_1$ absolute phase;
    acquiring at least two sets of complex k-space data from the MR signals, the at least two sets of complex k-space data including an RF pulse having encoded $B_1$ magnitude; and
    estimating a complex $B_1^+$ map of at least a portion of a transmit coil of the MM system directly from the acquired sets of complex k-space data, wherein the complex $B_1^+$ map includes both $B_1$ magnitude and $B_1$ absolute phase.

2. A magnetic resonance imaging (MRI) system for determining spatial distribution of magnitude and absolute phase of radio frequency (RF) transmit field $B_1^+$, comprising:
    a transmitting and receiving unit comprising at least one RF coil, wherein the transmitting and receiving unit is configured to:
        apply at least one pulse sequence using the at least one RF coil, the at least one pulse sequence being configured to excite precessing nuclear spins in magnetic resonance (MR) nuclei, the at least one pulse sequence comprising at least one RF pulse having encoded $B_1$ absolute phase and encoded $B_1$ magnitude, wherein the at least one RF pulse excites at on-resonance frequency, and
        detect a plurality of MR signals using the at least one RF coil, the MR signals representing nuclear MR signals arising from the precessing nuclear spins in the MR nuclei; and
    an MRI system controller operably coupled with the transmitting and receiving unit, the MM system controller comprising a processor and a memory, the memory having computer-executable instructions stored thereon that, when executed by the processor, cause the processor to:
        acquire at least two sets of complex k-space data from the MR signals, the at least two sets of complex k-space data including an RF pulse having encoded $B_1$ absolute phase,
        acquire at least two sets of complex k-space data from the MR signals, the at least two sets of complex k-space data including an RF pulse having encoded $B_1$ magnitude, and
        estimate a complex $B_1^+$ map of at least a portion of a transmit coil of the MRI system directly from the acquired sets of complex k-space data, wherein the complex $B_1^+$ map includes both $B_1$ magnitude and $B_1$ absolute phase.

3. The MM system of claim 2, wherein applying at least one pulse sequence further comprises applying a plurality of pulse sequences.

4. The MM system of claim 2, wherein the at least one RF pulse comprises a single RF pulse or a plurality of RF pulses.

5. The MM system of claim 4, wherein the at least one RF pulse comprises the plurality of RF pulses, and wherein the RF pulses include at least one RF pulse having encoded $B_1$ absolute phase and at least one RF pulse having encoded $B_1$ magnitude.

6. The MM system of claim 2, wherein each of the acquired sets of complex k-space data comprises full k-space or a portion of k-space.

7. The MM system of claim 2, wherein the at least one RF pulse excites at on-resonance and off-resonance frequencies.

8. The MM system of claim 2, wherein the at least one RF pulse comprises a rectangle RF pulse, a truncated-sinc RF pulse, a sinc RF pulse, a Gaussian RF pulse, an adiabatic RF pulse, a Hermite RF pulse, or a Shinnar-Le Roux RF pulse.

9. The MM system of claim 2, wherein the complex $B_1^+$ map is estimated using data in a k-space domain.

10. The MM system of claim 2, wherein the memory has further computer-executable instructions stored thereon that, when executed by the processor, cause the processor to:
    transform each of the at least two sets of complex k-space data including an RF pulse having encoded $B_1$ absolute phase into a respective image in an image domain; and
    transform each of the at least two sets of complex k-space data including an RF pulse having encoded $B_1$ magnitude into a respective image in the image domain, wherein the complex $B_1^+$ map of at least the portion of the transmit coil of the Mill system is estimated based on the respective images.

11. The MM system of claim 10, wherein estimating the complex $B_1^+$ map of at least the portion of the transmit coil of the MM system based on the respective images further comprises using at least one a double flip angle method, a dual pulse spin echo method, an actual flip angle imaging method, a steady state method, a dual refocusing echo acquisition mode (DREAM) method, a Bloch Siegert shift method, or a phase sensitive method.

12. The MM system of claim 10, wherein the memory has further computer-executable instructions stored thereon that, when executed by the processor, cause the processor to estimate a relationship between a complex MR signal of the respective images and the complex $B_1^+$ map, and wherein the complex $B_1^+$ map of at least the portion of the transmit coil of the Mill system is estimated based on the respective images and the relationship between the complex MR signal of the respective images and the complex $B_1^+$ map.

13. The MM system of claim 12, wherein the complex $B_1^+$ map is estimated using an analytic, empirical, or approximated solution of Bloch equations.

14. The MM system of claim 2, wherein estimating the complex $B_1^+$ map of at least the portion of the transmit coil of the MRI system further comprises estimating a k-space domain convolution kernel between k-space of the at least two sets of complex k-space data including an RF pulse having encoded $B_1$ absolute phase and the at least two sets of complex k-space data including an RF pulse having encoded $B_1$ magnitude.

15. The MM system of claim 14, wherein the k-space domain convolution kernel is estimated using a fitting algorithm.

16. The MM system of claim 14, wherein the memory has further computer-executable instructions stored thereon that, when executed by the processor, cause the processor to transform the complex $B_1^+$ map into an image domain.

17. The MM system of claim 2, wherein the at least two sets of complex k-space data including an RF pulse having encoded $B_1$ absolute phase or the at least two sets of complex k-space data including an RF pulse having encoded $B_1$ magnitude data are acquired using at least one of different MRI system configurations.

18. The MM system of claim 17, wherein the different MRI system configurations include at least one of different coil elements of a receive coil, different receive coils, or different gradient encoding strategies.

19. The MM system of claim 2, wherein the MRI system further comprises a plurality of RF transmit channels or elements, and wherein the at least two sets of complex k-space data including an RF pulse having encoded $B_1$ absolute phase or the at least two sets of complex k-space data including an RF pulse having encoded $B_1$ magnitude are acquired using an acquisition pulse sequence that is repeated a plurality of times using different ones or combinations of the RF transmit channels or elements for respectively corresponding different acquisition pulse sequences.

20. The MM system of claim 2, wherein the memory has further computer-executable instructions stored thereon that, when executed by the processor, cause the processor to store the complex $B_1^+$ map.

21. The MRI system of claim 2, wherein the encoded $B_1$ absolute phase is obtained by modulating the absolute phase using one or more transmit coils or phase modulations of each element of a multiple transmit coil.

* * * * *

UNITED STATES PATENT AND TRADEMARK OFFICE
CERTIFICATE OF CORRECTION

PATENT NO. : 11,047,935 B2
APPLICATION NO. : 15/573918
DATED : June 29, 2021
INVENTOR(S) : Jinghua Wang et al.

Page 1 of 2

It is certified that error appears in the above-identified patent and that said Letters Patent is hereby corrected as shown below:

In the Claims

Column 25, Line 43 for Claim reference numeral '1', "transmit coil of the MM system directly from the" should read --transmit coil of the MRI system directly from the--

Column 25, Line 66 for Claim reference numeral '2', "transmitting and receiving unit, the MM system con-" should read --transmitting and receiving unit, the MRI system con- --

Column 26, Line 18 for Claim reference numeral '3', "The MM system of claim 2, wherein applying at least" should read --The MRI system of claim 2, wherein applying at least--

Column 26, Line 21 for Claim reference numeral '4', "The MM system of claim 2, wherein the at least one RF" should read --The MRI system of claim 2, wherein the at least one RF--

Column 26, Line 23 for Claim reference numeral '5', "The MM system of claim 4, wherein the at least one RF" should read --The MRI system of claim 4, wherein the at least one RF--

Column 26, Line 28 for Claim reference numeral '6', "The MM system of claim 2, wherein each of the" should read --The MRI system of claim 2, wherein each of the--

Column 26, Line 31 for Claim reference numeral '7', "The MM system of claim 2, wherein the at least one RF" should read --The MRI system of claim 2, wherein the at least one RF--

Column 26, Line 33 for Claim reference numeral '8', "The MM system of claim 2, wherein the at least one RF" should read --The MRI system of claim 2, wherein the at least one RF--

Column 26, Line 37 for Claim reference numeral '9', "The MM system of claim 2, wherein the complex $B_1^+$" should read --The MRI system of claim 2, wherein the complex $B_1^+$--

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,047,935 B2

Column 26, Line 39 for Claim reference numeral '10', "The MM system of claim 2, wherein the memory has" should read --The MRI system of claim 2, wherein the memory has--

Column 26, Line 49 for Claim reference numeral '10', "the transmit coil of the Mill system is estimated based" should read --the transmit coil of the MRI system is estimated based--

Column 26, Line 51 for Claim reference numeral '11', "The MM system of claim 10, wherein estimating the" should read --The MRI system of claim 10, wherein estimating the--

Column 26, Line 53 for Claim reference numeral '11', "of the MM system based on the respective images further" should read --of the MRI system based on the respective images further--

Column 26, Line 59 for Claim reference numeral '12', "The MM system of claim 10, wherein the memory has" should read --The MRI system of claim 10, wherein the memory has--

Column 26, Line 65 for Claim reference numeral '12', "coil of the Mill system is estimated based on the respective" should read --coil of the MRI system is estimated based on the respective--

Column 27, Line 1 for Claim reference numeral '13', "The MM system of claim 12, wherein the complex" should read --The MRI system of claim 12, wherein the complex--

Column 27, Line 4 for Claim reference numeral '14', "The MM system of claim 2, wherein estimating the" should read --The MRI system of claim 2, wherein estimating the--

Column 27, Line 12 for Claim reference numeral '15', "The MM system of claim 14, wherein the k-space" should read --The MRI system of claim 14, wherein the k-space--

Column 27, Line 15 for Claim reference numeral '16', "The MM system of claim 14, wherein the memory has" should read --The MRI system of claim 14, wherein the memory has--

Column 27, Line 19 for Claim reference numeral '17', "The MM system of claim 2, wherein the at least two" should read --The MRI system of claim 2, wherein the at least two--

Column 28, Line 1 for Claim reference numeral '18', "The MM system of claim 17, wherein the different" should read --The MRI system of claim 17, wherein the different--

Column 28, Line 5 for Claim reference numeral '19', "The MM system of claim 2, wherein the MRI system" should read --The MRI system of claim 2, wherein the MRI system--

Column 28, Line 15 for Claim reference numeral '20', "The MM system of claim 2, wherein the memory has" should read --The MRI system of claim 2, wherein the memory has--